United States Patent
Ruiz et al.

(10) Patent No.: US 6,436,093 B1
(45) Date of Patent: Aug. 20, 2002

(54) CONTROLLABLE LIQUID CRYSTAL MATRIX MASK PARTICULARLY SUITED FOR PERFORMING OPHTHAMOLOGICAL SURGERY, A LASER SYSTEM WITH SAID MASK AND A METHOD OF USING THE SAME

(76) Inventors: Luis Antonio Ruiz; Eduardo Matallana, both of Centro Oftalmologico Colombiano Carrera 20 No. 85-11, Pisos 5o.-6o., Santafe de Bogota, D.C. (CO)

( * ) Notice: Subject to any disclaimer, the term of this patent is extended or adjusted under 35 U.S.C. 154(b) by 32 days.

(21) Appl. No.: 09/598,226

(22) Filed: Jun. 21, 2000

(51) Int. Cl.$^7$ ............................................... A61B 18/20
(52) U.S. Cl. ............................................... 606/5; 606/4
(58) Field of Search ........................................ 606/5, 4

(56) References Cited

U.S. PATENT DOCUMENTS

| | | | |
|---|---|---|---|
| 3,096,767 A | | 7/1963 | Gresser et al. |
| 4,245,883 A | | 1/1981 | Johnson et al. |
| 4,505,539 A | | 3/1985 | Auracher ................. 350/96.15 |
| 4,605,913 A | | 8/1986 | Pfleiderer et al. |
| 4,732,148 A | | 3/1988 | L'Esperance, Jr. ....... 128/303.1 |
| 4,733,369 A | | 3/1988 | Bogner |
| 4,856,513 A | | 8/1989 | Muller .................... 128/303.1 |
| 4,911,711 A | | 3/1990 | Telfair el al. ................... 606/5 |
| 4,917,486 A | | 4/1990 | Raven et al. ............... 351/221 |
| 4,994,058 A | | 2/1991 | Raven et al. ................... 606/5 |
| 5,105,215 A | | 4/1992 | Liu ............................. 355/40 |
| 5,207,668 A | | 5/1993 | L'Esperance, Jr. ............. 606/5 |
| 5,208,437 A | * | 5/1993 | Miyauchi et al. ...... 219/121.67 |
| 5,219,343 A | | 6/1993 | L'Esperance, Jr. ............. 606/5 |
| 5,279,932 A | | 1/1994 | Miyasaka et la. ........... 430/495 |
| 5,303,709 A | | 4/1994 | Dreher et al. ............... 128/665 |
| 5,312,320 A | | 5/1994 | L'Esperance, Jr. ............. 606/5 |
| 5,314,422 A | | 5/1994 | Nizzola |
| 5,395,356 A | | 3/1995 | King et al. |
| 5,520,679 A | | 5/1996 | Lin ............................... 606/5 |
| 5,556,395 A | * | 9/1996 | Shimmick et al. ............. 606/4 |
| 5,651,784 A | * | 7/1997 | Klopotek ....................... 606/5 |
| 5,703,709 A | * | 12/1997 | Mori et al. .................. 359/196 |
| 5,734,065 A | | 3/1998 | Saika |
| 5,735,843 A | * | 4/1998 | Trokel ........................... 606/5 |
| 5,742,362 A | | 4/1998 | Chikamichi |
| 5,747,772 A | * | 5/1998 | Matsumura et al. ... 219/121.85 |
| 5,871,879 A | | 2/1999 | Vanlinden et al. |

(List continued on next page.)

FOREIGN PATENT DOCUMENTS

| | | | | |
|---|---|---|---|---|
| GB | 417952 | * | 3/1990 | ........... B23K/26/06 |
| WO | WO 99/62397 | | 12/1999 | |

OTHER PUBLICATIONS

"Preparation of Polymer–Dispersed Liquid Crystals", Publication Date not known, Pulled from the Internet on Jun. 17, 2000, http://abalone.cwru.edu/tutorial/enhanced/files/pdlc/prep/prep.htm.

(List continued on next page.)

Primary Examiner—Linda C. M. Dvorak
Assistant Examiner—Henry M. Johnson, III
(74) Attorney, Agent, or Firm—Smith, Gambrell & Russell LLP

(57) ABSTRACT

A system and method particularly suited for controlled ablation of the cornea, using ultraviolet laser radiation, with the cornea sculpturing action resulting from a computer driven digital programmed distribution of excimer flux density across a controllable liquid crystal matrix mask to achieve a desired volume and shape of ablation for the correction of the curvature of the cornea. The optical mask, in one embodiment, is based on an arrayable matrix of individual optical pixel cells with two optical states between fully transparent to fully opaque or mirror like to the UV light. The system provides a highly versatile system for correcting known corneal defects in both regular and irregular corneas by simply executing computer customized patterns in very short time and with great precision and detail.

71 Claims, 10 Drawing Sheets

U.S. PATENT DOCUMENTS

| | | |
|---|---|---|
| 5,877,833 A | 3/1999 | Schraivogel et al. |
| 5,894,338 A | 4/1999 | Miehle et al. ............... 351/206 |
| 5,905,590 A | 5/1999 | Van Der Sluis et al. .... 359/275 |
| 5,917,890 A | 6/1999 | Brotman et al. |
| 5,942,136 A | 8/1999 | Mori et al. |
| 5,946,510 A | 8/1999 | Kobayashi et al. ......... 396/380 |
| 5,970,187 A | 10/1999 | Notten et al. |
| 5,999,152 A | 12/1999 | Liao et al. ..................... 345/87 |
| 6,054,969 A | 4/2000 | Haisma |
| 6,160,603 A | 12/2000 | Tanaka et al. |
| 6,184,917 B1 * | 2/2001 | Chiba et al. ................ 347/256 |

OTHER PUBLICATIONS

"Applications of PDLCs", Publication date not known, Pulled from the internet on Jun. 17, 2000, http://abalone.cwru.edu/tutorial/enhanced/files/pdlc/apps/apps.htm.

"Introduction to Polymer–Dispersed Liquid Crystals", Publication date not known, Pulled from the internet on Jun. 17, 2000, http://abalone.cwru.edu/tutorial/enhanced/files/pdlc/intro/intro.htm.

"Electrochromic Materials and Systems", Publication date not known, Pulled from the internet on May 30, 2000, http://techfac.uni–kiel.de/matwis/ionik/topics/ec.htm.

"Liquid Crystal Displays", Publication date not known, Pulled from the internet on Jun. 13, 20000, http://stefan.www.media.mit.edu/people/stefan/liquid–crystals/node3.html.

"Super TFT LCD Module", Publication date not known, Pulled from the internet on Jun. 13, 2000, http://www.hitachi.co.jp/Div/mobara/enc/3_2_1.htm.

"Nanocrystalline Electrochromic devices", Publication date not known, Pulled from the internet on May 15, 2000, http://dcwww.epfl.ch/lpi/electr.html.

"Electrochromism", Publication date not known, Pulled from the internet on May 30, 2000, http://info.lut.ac.uk./department/cm/mortimer.html.

"Materials, Organic and Polymer", Publication date not known, Pulled from the internet on May 30, 2000, http://www.chem.ufl.edu/~ortega/reynolds.html.

* cited by examiner

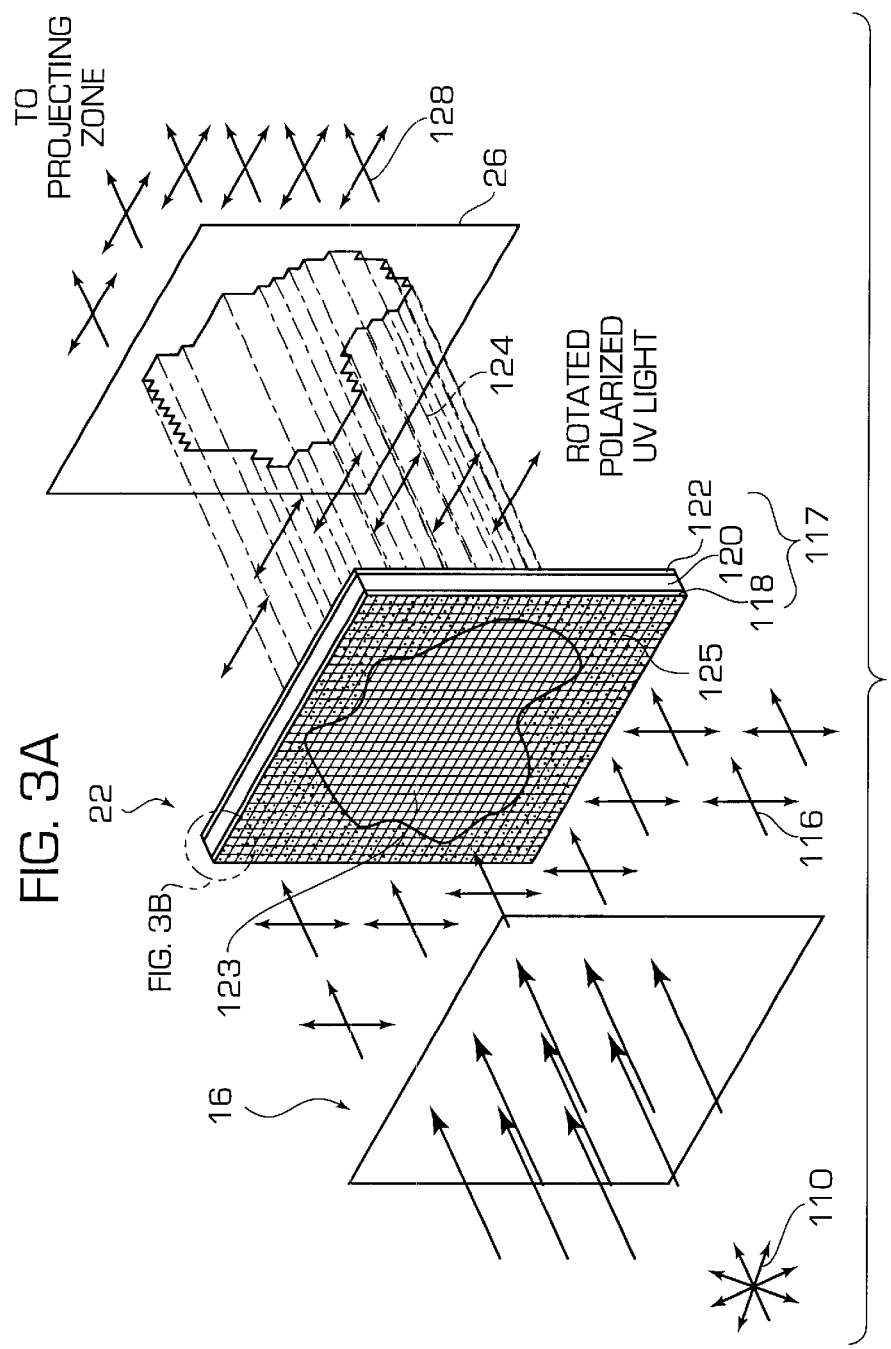
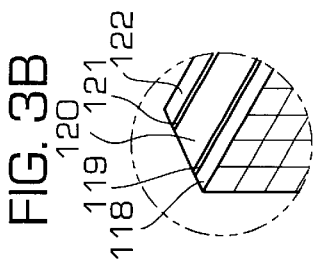
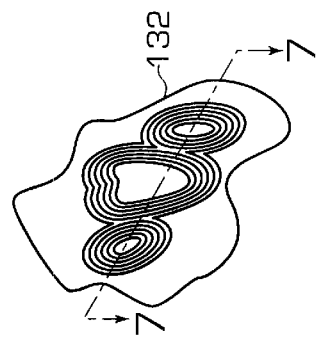

OFF-STATE

ON-STATE

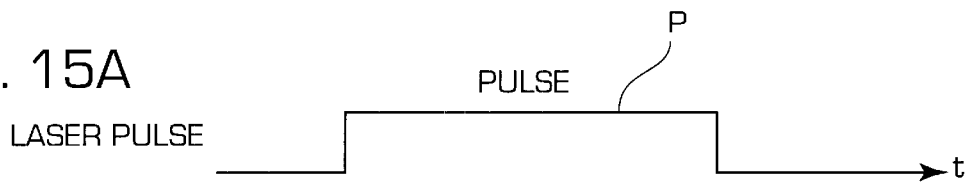
FIG. 15A  LASER PULSE
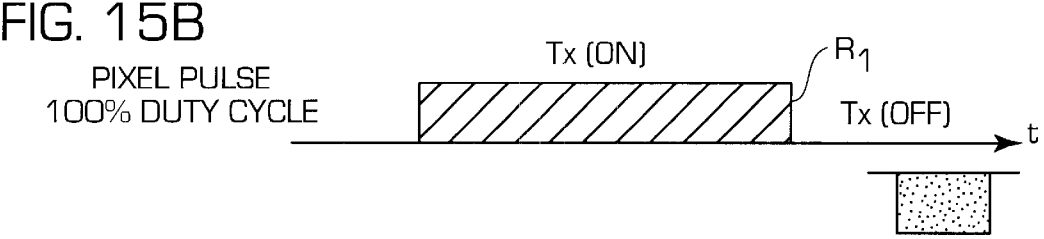
FIG. 15B  PIXEL PULSE 100% DUTY CYCLE
FIG. 15C  PIXEL PULSE 50% DUTY CYCLE
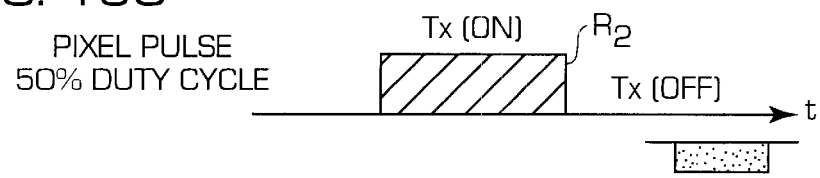
FIG. 15D  PIXEL PULSE 25% DUTY CYCLE
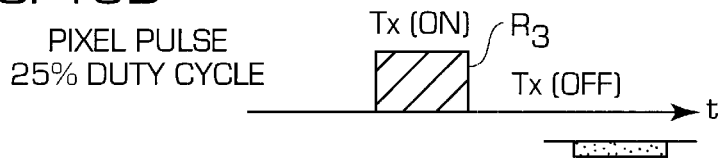
FIG. 15E  PIXEL PULSE 12.5% DUTY CYCLE
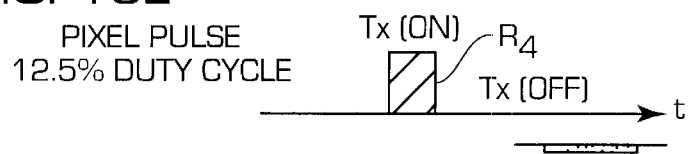
FIG. 15F
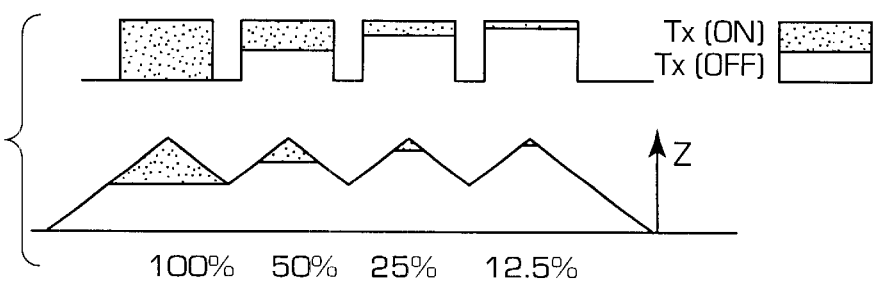

CONTROLLABLE LIQUID CRYSTAL MATRIX MASK PARTICULARLY SUITED FOR PERFORMING OPHTHAMOLOGICAL SURGERY, A LASER SYSTEM WITH SAID MASK AND A METHOD OF USING THE SAME

FIELD OF THE INVENTION

The present invention relates to a controllable liquid crystal matrix (patternable) mask for controlling ultraviolet laser energy, and a system which involves the use of the controllable liquid crystal matrix mask for use in, for example, an ophthalmic surgical system such as an excimer laser system for contouring the cornea through controlled ablation of the cornea with penetration into the stroma and volumetric removal of corneal tissue whereby the ablated corneal surface is characterized by a sculptured new curvature having improved optical properties.

BACKGROUND OF THE INVENTION

Various surgical techniques for reprofiling of the corneal surface have been proposed as described in, for example, L'Esperance, U.S. Pat. No. 4,732,14; J. T.Lin, U.S. Pat. No. 5,520,679; David F Muller, U.S. Pat. No. 4,856,513; Kristian Hohia, U.S. Pat. No. 5,520,679. Each of these patents is incorporated by reference herein.

In practice there are two basic techniques to ablate and remove a set volume of tissue in the cornea and they are:

1) a scanning technique that uses a small flying laser spot between 1–2 mm in diameter and requires thousands of pulses to do the surgery; and 2) a large spot beam technique wherein a laser beam of around 8 mm in cross-section is used in conjunction with an erodible mask or a moving, blocking mask to ablate and which generally requires, on average, a few hundred pulses to achieve the desired ablation.

The main advantage of a flying laser spot technique is the ability to readily execute irregular patterns. However, the flying laser spot technique suffers from the drawback of generally requiring longer surgical times to execute the desired ablation pattern both from the standpoint of the number of pulses required and the overlapping requirement to ensure coverage of the ablated area. Any increase in the length of time required to carry out the laser ablation process can lead to longer corneal exposure time and corresponding medical concerns such as cornea dehydration which can lead to poorer healing, poorer visual acuity and, in general, longer post operative recovery times. A longer time period in which a laser is operated per patient also leads to a decrease in the useful life of the laser and an increase in service requirements. In addition to the time delay associated with a flying spot laser technique, there is also the problem of ridges and valleys being formed due to overlapping that will prevent a highly smooth and polished ablation. Flying laser spot techniques place greater stress on the laser cavity and the optical train components due to high repetition and rate requirements.

A large beam spot system does allow for more rapid application of the desired energy (including the avoidance of the degree of overlapping involved in a randomly or non-randomly applied, partially overlapping flying spot system) and typically places less strain on the laser equipment, but does not have the irregular pattern versatility provided with a flying spot system. Also, if mechanically moving components are relied upon as the means for blocking or allowing through the laser beam (e.g., an iris or rotating or sliding aperture plate), then the problems of mechanical wear, potential jamming or breakdown arise.

Attempts have been made to provide masks that operate with a large beam application including EP 0 417 952 to Rose et al. which uses a stacked set of binarily weighted masks (A to H) on a cornea intended for sculpturing. A proposed system such as this one suffers from a variety of drawbacks such as the time consumption involved in stacking and developing the mask sets and the increased potential for error brought about by a system using so many different stacked mask components.

Another example of the use of large beam application is found in U.S. Pat. No. 4,994,058 which describes a supported or contact type mask presenting a predetermined resistance to the beam such as through use of a different height erodible mask or by varying the composition of the plastic material making up the mask. A mask arrangement such as this avoids the complications of a scanning laser, but is very limited from the standpoint of having to prepare a new mask for each patient and, with respect to an erodible mask, not having the benefit of being able to test the pattern on a test strip or the like without destroying the mask. In use of an erodible mask there is also heavy reliance on chosen material consistency.

SUMMARY OF THE INVENTION

The present invention is directed at providing a controllable, patternable liquid crystal mask that is particularly well suited for use with ultraviolet electromagnetic energy utilized in an ophthamological surgical procedure such as a photo refractive keratectomy (PRK); photo therapeutic karatectomy (PTK); and a laser in-situ keratomileusis (LASIK) surgical procedure for resculpturing the exposed cornea of an eye. Accordingly, the present invention is directed at providing a controllable patternable mask system, an ophthalmic laser surgery system with said controllable mask system, and a method of using the same. The apparatus and method of the present invention is particularly well suited for ablating a corneal surface using a laser in the ultraviolet spectrum to achieve extremely smooth and precise ablation surfaces with a mask system that can be repeatedly used for different patient ablation requirements. The mask is used with a large beam spot (e.g., 6–8 mm) which covers the entire projected surface on a cornea and thus avoids the time delays associated with a flying spot beam as well as ridge and valley formation. In addition to multi-patient use, the present invention avoids the delays associated with the prior art with respect to forming or assembling the mask. Moreover, the present invention provides a system which can achieve repeated high precision or registration between the planned or predetermined ablation volume to be removed and the actual ablation volume removed so as to better enable a surgeon to achieve desired levels of eyesight corrections. Also, the volumetric ablation patterns to be removed can involve highly irregular or regular configurations, as an object of the present invention is to provide a system which facilitates the execution of a surgical procedure on highly irregular individual customized patterns on a patient's cornea in addition to more regular volumetric patterns.

Furthermore, the arrangement of the present invention provides a system that can achieve a customized volumetric ablation pattern based on, for example, a stored, ophthamological patient data set (e.g., an ablation data set as described in U.S. patent application Ser. No. 09/267,926 filed Mar. 10, 1999 by Dr. Luis Ruiz which application is incorporated herein) which data set is developed by a measuring instrument such as a topographer or aberrometer and, under the present invention, is provided to a processor for input to the mask system via a digital interface, for example. The matrix mask system of the present invention includes an active liquid crystal matrix mask which receives expanded, polarized laser energy and, based on the processed patient data, controls the energy pattern that exits in the mask for sculpturing the desired ablation pattern on the cornea.

Under the present invention, the ablation pattern data set is processed by a processor such as the laser's main computer which communicates with the mask via an interface or the like to provide corresponding commands to activate the matrix mask. For example, in one embodiment of the invention, the transmission pixel pattern of the mask is individually controlled by the computer and is synchronized with the pulse rate of the main excimer laser. In this way, any regular or irregular ablation volume can be removed by ablating with each pulse of the large beam a set depth (based to the laser characteristics such as laser energy and density) corresponding with the matrix pattern set for that pulse. By changing the mask's matrix pixel pattern with each large beam pulse a different ablation configuration (or the same) can be removed to achieve the desired total pattern, volume and depth.

With an excimer laser working in the ultraviolet energy spectrum, the components of the optical train are subjected to relatively high energy flux levels. Under the present invention, the large beam is preferably expanded with a beam expander or the like positioned upstream from the active matrix mask to lower the energy density per area received by the pixels of the mask. This will avoid premature destruction of the mask. The non-blocked, transmitted portions of the large beam containing the latent image determined by the active mask are then compressed with a focusing lens or the like to achieve the desired ablation profile.

Prior to reaching the liquid crystal material of the liquid crystal active mask, the laser beam is first polarized with a polarizer and, after exiting the liquid crystal material, the beam with the latent image passes through a second polarizer also known as an analyzer to the ablation plane or surface. The position of the expander/collimator can be either before or after the first polarizer, with the same being true for the relationship between the focusing lens and second polarizer.

Thus, the present invention preferably features a controlled ablation of the cornea, using ultraviolet laser radiation to achieve a sculpturing action derived from a computer driving a digital programmable distribution of excimer flux density across an ultraviolet computer controllable liquid crystal matrix mask as to achieve a desired volume and shape of the ablation for the correction of the curvature of the cornea.

The computer controllable liquid crystal matrix mask is based on a matrix array (matrix is used in a broad sense to involve any pattern suited for forming a desired ablation pattern on the ablation plane or surface) of individual optical liquid crystal pixel cells with optical states between fully transparent to fully opaque or mirror like to the UV light. (Preferably, for high resolution purposes, each cell is individually controlled although groups of interlinked pixels could be controlled by the processor as a group unit to present a combined transmission state. Hence, the term "pixel" or "pixel cells" is used herein unless otherwise indicated to include single or groups of similarly controlled pixel element groups.) As noted, the ultraviolet computer controllable liquid crystal matrix mask is based on transmission of polarized light through the mask device, the transmission of polarized light through each individual pixel is preferably controlled by an electrical voltage and a time duty cycle. In one embodiment of the invention the voltage is switched or adjusted to have the pixels either in a fully transparent or fully blocking mode with the pixel switching timing being synchronized with the laser pulse rate. In addition thereto, the frequency duty cycle per pixel can be adjusted or varied with relation to the laser pulse cycle of the main laser to achieve multiple on and off states of transmission during the main laser pulse cycle so as to control the maximum state of ablation during that main pulse cycle.

Preferably the active matrix liquid crystal mask is based on the twisted nematic (TN) natural physical effect of liquid crystals for controlling light transmission. The principle of the active matrix mask device of the present invention is as follows: Unpolarized excimer light enters a first polarizer and emerges polarized, the polarized light (UV electromagnetic radiation) is sent into the liquid crystal mask which comprises many pixels. When no voltage is applied to a pixel, the polarization vector of the incoming light is rotated a quarter turn/90° by the liquid crystal molecules through the TN natural physical effect. A second polarizer (or analyzer) placed at the output side of the liquid crystal cell is used to transmit either the light (normally on) or reject the light (normally off). When a proper voltage is applied to the electrodes of the pixel, the TN effect disappears (as the liquid crystals tend to orient with the electric field resulting in a loss of their natural twisting function) and the polarization vector of the polarized light is unchanged. The light will therefore be rejected (off) or transmitted (on) by the second output polarizer, depending on whether the device is normally on or off, respectively.

Accordingly, the crystal molecules within the pixel cells act as an optical wave guide by rotating the polarization vector of the UV light which is to reach the second polarizer. If the second polarizer is set to have a polarization vector coincident with that of the twisted polarized UV light, then the cell will be "on" when no electric field is imposed as the cell allows the UV light to transmit through it to the desired ablation surface. In this state the liquid crystal pixel cell is transparent since the second polarizer has a vector coincident with the twisted polarized UV light. With this arrangement, the passage of non-twisted UV polarized light due to the generation of an electric field will be blocked and the cell will appear dark.

If, instead, the second polarizer is arranged as to be non-coincident with the twisted polarizer UV light vector, then the second polarizer will act to prevent transmission of the twisted polarized UV light and will be "off" and the cell will appear non-transparent. With this arrangement, the second polarizer is arranged to be coincident with the untwisted polarized UV light (made possible by an electric field generation) such that the un-twisted light energy passes through the second polarizer for transmission to the ablation surface) when an energy field is generated. Each pixel can be turned on or off independently by the active control of the voltage across it.

A preferred embodiment of the present invention features a mask system for controlling the transmission of ultraviolet electromagnetic radiation (UV) that comprises a first UV grade polarizer, a liquid crystal matrix mask having a plurality of individual pixel cells with individually adjustable states of transmission with respect to polarized UV electromagnetic radiation received from said first UV grade polarizer, and a second UV grade polarizer also known as the analyzer positioned downstream for receipt of polarized UV electromagnetic radiation transmitted by the liquid crystal matrix mask. The active mask of the mask system is preferably in communication with control means, such as a processor and a digital interface or the like, for controlling relative transmission states amongst the individual pixels in the matrix array.

The mask system of the present invention also preferably includes a beam expander/collimator assembly which is positioned in line with the UV electromagnetic radiation travel path and is positioned upstream with respect to the liquid crystal material of the liquid crystal mask. The beam expander/collimator is also preferably positioned downstream of said first polarizer and upstream of the liquid crystal material with respect to UV electromagnetic radiation travel. The mask system also preferably comprises a focusing lens that is positioned downstream of the liquid crystal material and upstream of the second polarizer, again with respect to UV electromagnetic radiation travel. In addition, for desired laser designs for use in the present invention it is further preferable to have a turning mirror positioned within the optical path leading to the active mask and preferably between the expander/collimator assembly and the active mask with respect to laser beam travel.

As noted, in a preferred embodiment, the liquid crystal mask includes a twisted nematics liquid crystal material. In addition, the first and second polarizers are preferably physically separated from the liquid crystal mask. This mask embodiment also comprises an inner and outer UV grade substrate (e.g., UV grade synthetic fused silica or sapphire) with deposited electrode material on an inner side so as to provide a sandwiching effect with respect to the liquid crystal material in between the two electrode devices. Also, the first and second polarizers are preferably designed for peak polarization of UV electromagnetic radiation at 193 nm.

The aforementioned processor interfaced with the mask for controlling relative transmission states between said individual pixel cells preferably includes means for shifting a pattern formed in said array to have the shifted pattern position correspond with a shift in position of a substrate to receive UV electromagnetic radiation transmitted by the mask. As one example, the means for shifting the pattern works in conjunction with an eye tracker system so as to shift the pixel pattern in conjunction with a detected shift in the cornea position of the eye detected by an eye tracker.

The mask system of the present invention preferably features a mask with a pixel array having at least 512×512 resolution with each pixel size being 125μ or less. Even more preferably, the pixel array is at least 1024×1024 in number and the pixel size 100μ or less.

In one embodiment of the invention, the individually adjustable states of transmission are limited to fully transmitting "on" and fully blocking "off." In another embodiment of the invention, the mask, which is designed for receipt of laser pulses, further comprises pixel switching timing means for controlling the timing of pixel switching between different on and off states (when desired). In one embodiment, switching takes place in a one-to-one relationship with respect to laser pulses received by the mask. That is, at some time between each pulse, pixel switching activity takes place to alter the pattern presented to the incoming beam of the next pulse.

The mask system of the present invention can further include a pixel switching timing means for timing individual pixel switching between different states and which sets a duty cycle for individual pixels at a duty cycle of from 0% (off for full pulse transmission period) to 100% (on for full pulse transmission period) with at least one or more set pixel duty cycle(s) being at an intermediate value(s) falling between 0 to 100% with respect to the pulse cycle of the main laser beam.

The present invention is also directed at a laser system for ophthamological surgery which comprises a laser, and a liquid crystal mask having a plurality of individual pixel cells positioned for receiving a laser beam output by the laser. The individual pixel cells of the mask have adjustable transmission states for forming a transmission pattern with respect to the laser beam output by the laser. In an embodiment of the invention, a first UV grade polarizer is positioned upstream (with respect to laser beam travel) to the pixels while a second polarizer is positioned downstream (with respect to laser beam travel) from the pixels. In this embodiment, a twisted nematic liquid crystal material is also preferred. The first and second polarizers are provided with a common polar vector direction in one embodiment, while in an alternate embodiment the first and second polarizers have a non-common or shifted polar vector direction.

The laser system of the present invention further preferably has an expander/collimator assembly that is positioned downstream with respect to said first polarizer and upstream with respect to the liquid crystal material of said matrix, together with a focusing member positioned downstream from the liquid crystal mask with the mask having first and second substrates of a UV grade material, and together with a turning mirror for redirecting an expanded large spot beam to the matrix in a perpendicular relationship.

The focusing member is designed to focus a latent image pattern formed by the mask onto a projected surface wherein transmitted UV energy of adjacent transmitting pixels is compressed into a minimum overlap relationship (e.g., one involving less than 5% or and more preferably less than 1% overlap of the adjacent ablated regions generated by the pixel cells) or a minimized spacing relationship (e.g., one involving less that 5% spread apart and more preferably less than 1% spread), or an essentially abutting relationship (of ±0.75% overlap/spacing apart).

The laser system of the present invention preferably includes directing means for directing pixel transmission state controls to said mask wherein said directing means includes a processor and an interface linking said processor and mask. The processing means preferably further comprises means for processing acquired volumetric ablation volume data and basing pixel control outputs to said matrix on the processed acquired volumetric ablation volume data. The laser system also further includes means for acquiring three dimensional volumetric ablation pattern data such as means for receiving corneal ablation data based on topographical and/or aberrometer measurements.

In a preferred embodiment of the invention, the processor further includes means for segmenting acquired corneal volumetric ablation pattern data into a plurality of matrix segments and means for determining a desired individual pixel transmission status arrangement for respective segments of said acquired volumetric ablation pattern. Preferably all processor functions are handled by a central computer in the laser system of the present invention although sub-processor(s) or sub-processor group(s) are also suited for use in the present invention. The system of the present invention also preferably comprises means for sequentially changing a pixel array pattern based on respective, determined pixel transmission statuses for the individual ablation segments stored in a memory stack, such as a top to bottom or bottom to top memory stack sequence with respect to the ablation segments derived from the acquired volumetric ablation pattern.

As the liquid crystal material matrix features a deposited electrode plating or the like on the UV grade substrates, the processor of the laser system is in communication with the mask via an interface device such as a digital interface device for converting digital information to individual pixel voltage signals. The laser system of the present invention preferably also includes means for determining a transmission switching rate for individual pixels of said array based on a duty cycle correlated with a laser pulse period of the laser. For example, individual pixels of the mask are assigned one of two states, either a duty cycle of 0% (no transmission) state during the pulse period state or a 100% (full transmission) state during the pulse period state. In an alternate embodiment, at least some of the individual pixels of the mask are assigned a duty cycle that is intermediate the 0% (no-transmission) state during the pulse period and a 100% (full transmission) state during the pulse period.

A preferred embodiment of the laser system further includes an eye tracker and a processing device which is in communication with both said eye tracker and said mask, and said processing device includes means for implementing a switch or change over in a transmission state of individual pixel cells to shift a pattern defined by pixel cells in said mask from a first pattern position to a second pattern position in correspondence with a shift in location of a projected surface of an eye being monitored by said eye tracker. A similar means can be provided for monitoring and adjusting pixel positions for different types of substrates other than an eye which are subject to movement between laser pulses or mask refreshings.

The present invention is also directed at a method for ablating an eye cornea that comprises directing a polarized laser beam to a liquid crystal mask having a plurality of pixels with individually controllable pixel states, and directing "through" mask transmitted portions of the laser beam onto a corneal surface for sculpturing the corneal. The method of the present invention further includes altering a first pattern defined by said pixels into a second pattern between pulses of the laser to alter the ablation pattern on the cornea. A preferred method of the invention further comprises processing acquired volumetric ablation pattern data to provide pixel transmission state control signals to the individual pixels of the mask. Moreover, the present invention further comprises a method of monitoring a projected surface of the substrate to be ablated with means for monitoring and, with information obtained from the means for monitoring, shifting the pattern formed in the mask to compensate for a shifting in position of the projected surface prior to the next ablation energy application.

BRIEF DESCRIPTION OF THE DRAWINGS

FIG. 3A illustrates an embodiment of the active matrix mask controlling exposure of polarized UV light through a customized irregular pattern on the mask to the projecting zone.

FIG. 3B provides an enlarged view of a section of the active matrix mask in FIG. 3A.

FIG. 3C provides a topographical illustration of a volumetric ablation pattern.

FIG. 15A shows a time based depiction of the main laser's pulse.

FIG. 15B shows a time based depiction of a full "on" pixel transmission relationship with respect to the main laser pulse without intermediate states and at a 100% duty cycle.

FIG. 15C shows a time based transmission "on" setting for the switching between a first pixel state (overall or individual) and a second pixel state with the switched pixels being at a 50% duty cycle with respect to the main laser pulse period.

FIG. 15D shows a different (25%) duty cycle for the switching between pixel states (individual or overall) with respect to the main laser pulse period.

FIG. 15E shows a (12.5%) duty cycle for the switching between pixel states (individual or overall) with respect to the main laser pulse period.

FIG. 15F illustrates the relationship between a pixel provided with different duty cycle states and the relationship with the corresponding ablation.

DETAILED DESCRIPTION OF THE PREFERRED EMBODIMENT

Figure 1:
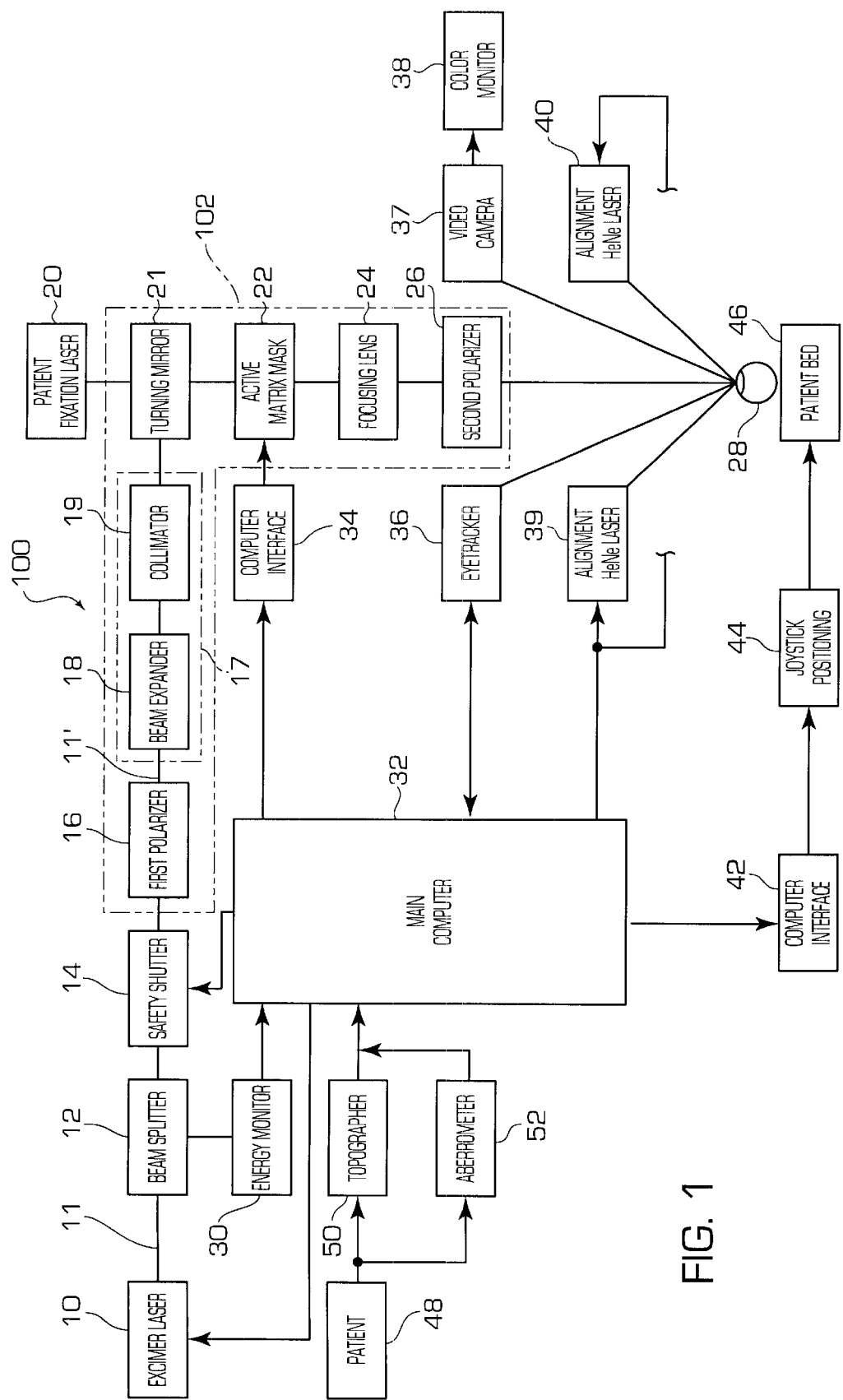
FIG. 1 is a general block diagram of a preferred embodiment of the ophthalmic laser surgery system of the present invention with controllable matrix mask system utilized therein.
Figure 2:
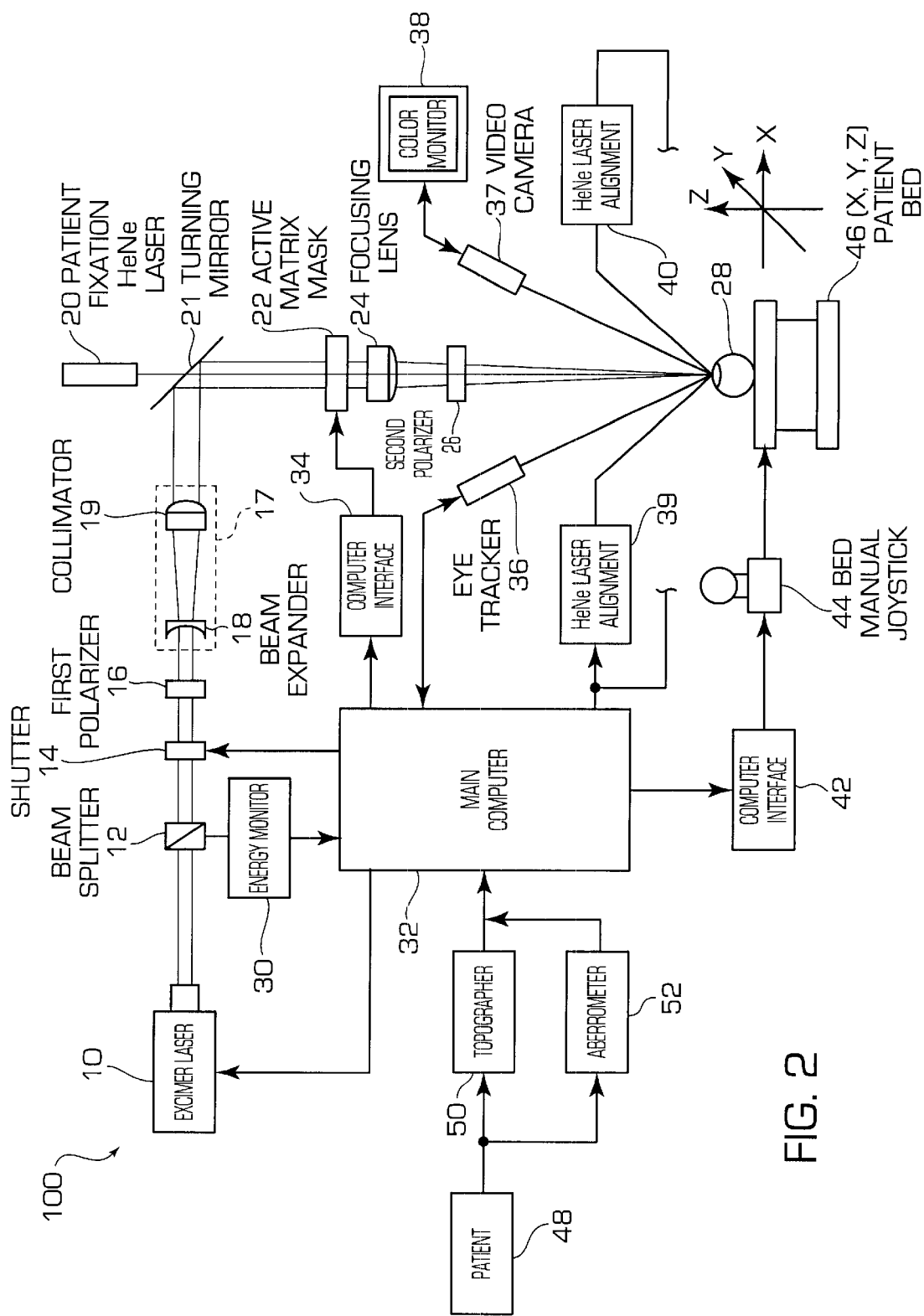
FIG. 2 is a general, schematic physical diagram of the ophthalmic laser surgery system of FIG. 1.

FIG. 1 shows a block diagram of a preferred embodiment of the ophthalmic laser surgery system 100 of the present invention, and FIG. 2 provides a schematic physical presentation of that which is shown in FIG. 1. As shown in FIGS. 1 and 2, a laser beam is delivered by laser 10, which is preferably an excimer laser outputting light at 193 nm although other ultraviolet energy levels suited for ablating corneal tissue can be relied upon.

The laser beam outputted by excimer laser 10 is a large spot laser beam. A suitable excimer laser is provided by a Lambda Compex Model 205 excimer laser manufactured by Lambda Physics GmbH, located in Gottinggen, Germany from which there can be achieved a circular beam with a diameter of 6 to 10 mm from the rectangular original beam shape of the excimer laser through optical treatment (e.g., a cylindrical and aspherical lenses). This excimer laser beam size is well suited for accommodating most eye configurations and the excimer laser preferably outputs a pulse in excess of 400 mj which is sufficient for corneal ablation despite losses in the optical train components particularly the first in line polarizer discussed below. An 8 mm diameter large beam with an energy level of 400 mj or higher is particularly well suited for the preferred applications of the present invention.

The large spot beam output 11 by the laser is passed through a beam splitter 12 where a small quantity of the UV light is reflected by the beam splitter to be input and measured by the energy monitor 30. The energy monitor 30 then inputs the monitored energy information to main computer or main processor 32 where a comparison is made between the actual energy being output by the laser and the desired energy level, and the processor directs an adjustment signal to the laser's voltage source to effect any adjustments needed to obtain the desired energy level at the laser head to maintain a constant energy level.

The UV light passing through the beam splitter is directed to safety shutter (14) preferably in the form of a mechanical, physical light beam blocking device. The safety shutter is placed "on" when the system is in surgical mode and is placed "off" in a blocking position whenever the processor receives an input from one of the laser system's components suggesting a device is not working within established parameters or upon an operator's activation of an emergency shut off.

During a non-shut off state of operation, the UV light beam 11 is directed to first UV grade polarizer optic 16 suited for handling the relatively high energy densities associated with the UV light beam 11 such as the preferred 193 nm. The first polarizer 16 which the light beam reaches is transparent to the ultraviolet light and is used to polarize the excimer laser beam such that the light beam exiting the polarizer oscillates on a defined plane (e.g., has a common polarization vector) according to the characteristics and orientation of the polarizer optic.

The polarized light beam 11' is then received by beam expander/collimator assembly 17 which includes beam expander 18 and collimator 19. Beam expander 18 provides a beam expansion function while collimator 19 functions to limit the degree of expansion to a predetermined level. Under the present invention, the beam expander/collimator assembly distributes and lowers the energy density per area of the polarized large beam 11' prior to the expanded beam being applied to the active matrix mask. Because UV light energy at the typical wavelength suited for corneal ablations (e.g., 193 nm) has relatively high energy levels, the expansion is helpful in prolonging the life of the liquid crystal active matrix mask 22 described in greater detail below.

The resulting expanded light is preferably reflected or redirected (due to the typical positioning of the laser head) by turning mirror 21 so as to travel in a straight line into a transverse relationship with the projecting zone or surface 28 (e.g., exposed corneal surface being ablated).

The light beam is then directed to the active matrix mask 22 which has a controllable, reusable liquid crystal pixel array with each pixel being individually controlled to vary the light beam transmission characteristics of each pixel.

FIG. 1 also shows, by way of dashed lines a preferred controllable matrix mask system 102 which comprises, in the illustrated embodiment, first polarizer 16, beam expander/collimator assembly 17, turning mirror 21 (desired for most system designs), liquid crystal matrix mask 22, focusing lens 24 and second polarizer 26.

FIG. 3A shows in greater detail a subsystem of controllable matrix mask system 102, which is the same as system 102 except with beam expander/collimator assembly 17, turning mirror 21 and focusing lens 24 not being present. This is illustrative of the possibility of positioning first polarizer 16 either upstream or downstream from beam expander/collimator assembly 17, to achieve its desired function although, from the standpoint of being able to use a reduced size polarizer, a location such as shown in FIG. 1 before beam expansion is preferred. The positioning of first polarizer 16 separate and distinct from the other optical components in the laser system 100 is also helpful from the standpoint of easier replacement of this first in line component of mask system 100. However, as shown in FIG. 3A, first polarizer can be positioned in direct sequential beam travel fashion with respect to the liquid crystal material and downstream of the expander/collimator assembly. The important thing being that the polarizer polarizes the light before the light passes through the liquid crystal material.

In FIG. 3A the unpolarized light beam from the excimer laser is directed through the first polarizer to produce polarized UV light 116 which oscillates along a common polar plane (shown, by way of illustration only, as a vertical plane in FIG. 3A). In the embodiment shown in FIG. 3A, the polarized light is then directed at active matrix mask 22.

With reference to FIGS. 3A and 3B, a description of a preferred embodiment of the active mask 22 is provided. Mask 22 comprises a multi-layer assembly 117 which includes first substrate plate 118 of, for example, UV grade synthetic fused silica (i.e., UVGSFS ($SiO_2$)) or sapphire. This transparent substrate plate is followed by a first, transparent electrode layer 119 which, in the illustrated embodiment, is the electrode layer 119 having the pixel electrode cells 125 (typically deposited) (FIGS. 5 and 6) and the (typically deposited) voltage lead lines 127 (FIGS. 5 and 6).

Liquid crystal material 120 is provided between first transparent electrode layer 119 and second transparent electrode layer 121, with the second electrode 121 layer in the illustrated embodiment being a full sheet electrode layer (with respect to the pixel electrode cells 125 outer peripheral border). Thus, upon application of a low level voltage (on or off) to the electrodes (depending on the preferred, preset condition) on each individual pixel cell, a desired pixel mode can be achieved due to a change in orientation of the liquid crystal material associated with the activated pixel. Preferably, the deposited 119 electrode layer is deposited directly on the substrate 118 as a thin layer of (ITO) indium-tin oxide or $SnO_2$ by means of conventional depositing techniques such as vacuum evaporation, chemical vapor deposition, electroplating, or other commonly known methods.

Figure 5:
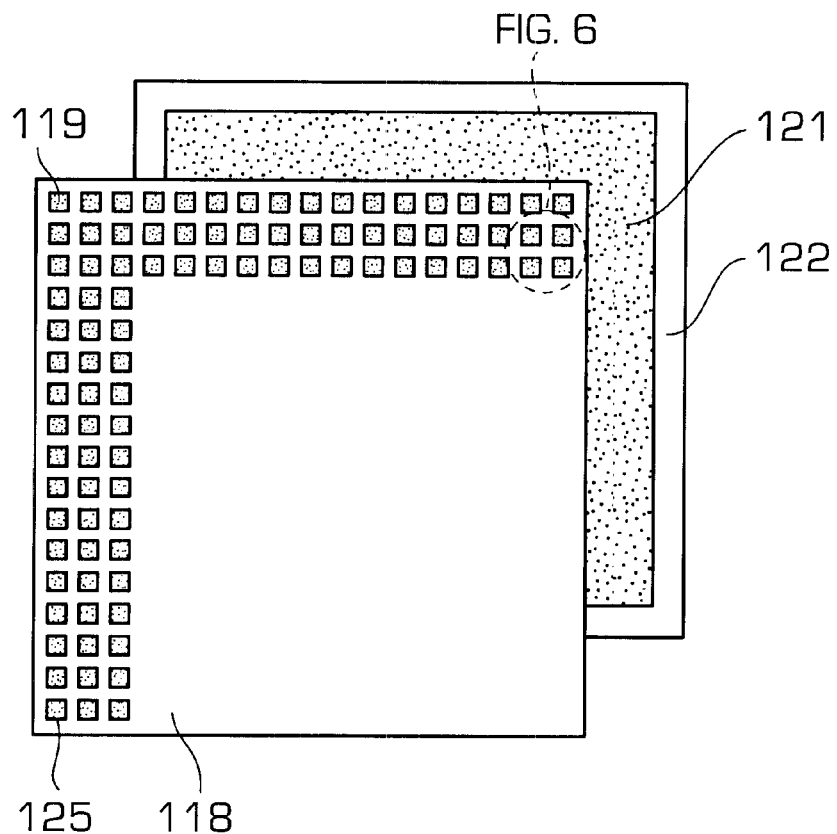
FIG. 5 shows an exploded view of a portion of the active liquid crystal matrix mask shown in FIG. 3A with the transparent electrode pixels being darkened to facilitate an explanation thereof.
Figure 6:
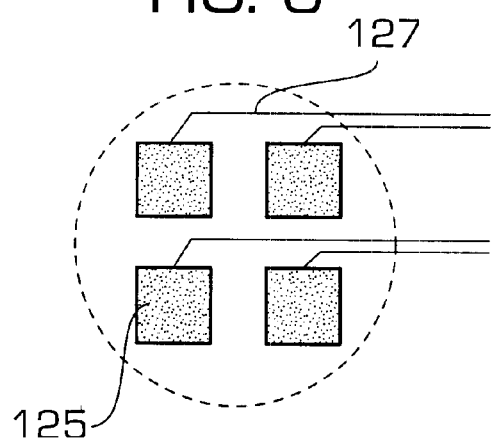
FIG. 6 shows an enlarged view of the circled segment in FIG. 5.

As shown in FIGS. 5 and 6, the pixel cells (only some shown for draftsman convenience) are preferably arranged in a square matrix which is sufficient in number to achieve the desired degree of ablation precision such as a 1024×1024 pixel array with a pixel size of 100$\mu$ or less being preferred, although other resolutions are also possible with lesser number pixel arrays (e.g., 512× 512) and larger pixel sizes (e.g., 100$\mu$ to 150$\mu$). In FIG. 5, the deposited electrode material is shown darkened to facilitate explanation, although the material is transparent in a preferred mask embodiment. Thus, in FIG. 5 the pixels defined by the pertinent pixel electrode material is visible through the transparent substrate 118. The transparent liquid crystal material which is normally sealed between the electrode layer is also not shown in FIG. 5.

FIG. 3A further illustrates irregular pixel latent pattern 123 formed in active matrix 22 which is differentiated by the lighter shaded pixel area 123 in the mask (transparent-transmission state) and the darker shaded pixel area 125 (non-transparent non-transmission). For illustrative purposes, there is provided in FIG. 3C, the total volumetric ablation pattern 132 with the three dimensional topography associated with the irregular pixel pattern 123. Each topography level representation preferably corresponds to a single volumetric ablation segment of the entire ablation volume (shown schematically as each ablation segment would, in a preferred embodiment, correspond with the ablation depth characteristic of the laser which, for a full duty cycle, is often around 0.21 $\mu$ to 0.25 $\mu$).

In a preferred embodiment, the liquid crystal material 120 provides a twisted nematics (TN) effect on the polarized light 116 passing through matrix 22. With a twisted nematic liquid crystal material, the polarization vector of the incoming light is rotated by a quarter turn ¼ (90 degrees) by the liquid crystal molecules through the natural physical twisted nematics effect produced by the liquid crystal molecules. In other words, liquid nematic substance 120 (typically sealed off by a peripheral frame structure surrounding or abutting the electrode material and sandwiched between the substrate supports) is used as a rotator layer and is placed inside between the two electrodes 119 and 121 as well as between the first and second substrates 118 and 122 and also between polaraizers 16 and 26. The second polarizer 26 is designed in one embodiment to have a polarization vector that is 90° offset from that of the first polarizer. In this preferred embodiment, when no voltage is applied on a pixel, the polarization vector of the incoming light is rotated by the liquid crystal molecules through the twisted nematic effect so as to have the rotated polarized light oriented for passage through the 90° offset second polarizer. Thus, the second polarizer, placed at the output side of the liquid crystal mask, is used to transmit the light (normally on).

On the other hand, with the first and second polarizers in a 90° offset relationship, when a proper voltage is applied to a pixel cell, the crystal liquid molecules tend to align with the electric field, such that the twisted nematic effect is lost and thus the polarization vector of the incoming light will be unchanged (i.e., not rotated). The light will therefore be rejected (off) by the output polarizer as its polarization vector is not aligned with the non-twisted UV energy. Alternatively, the first and second polarizers can be arranged to have their polarization vector initially aligned in which case the second polarizer will be normally off (the twisted light is blocked) and upon an electric field application the second polarizer will allow for transmission of the untwisted, polarized light traveling thereto.

Figure 4A:
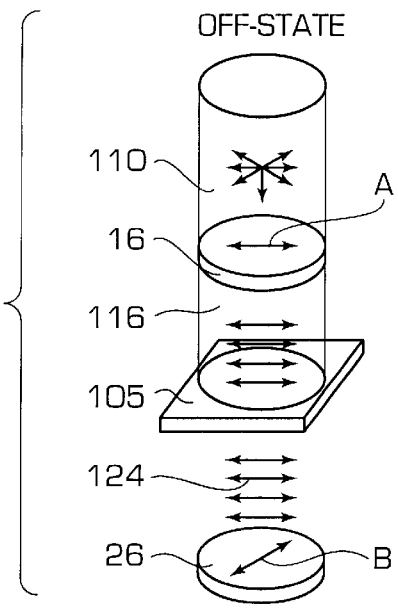
FIGS. 4A and 4B provide an optical representation of the on/off transmission states for a pixel cell within the active matrix mask with FIG. 4A illustrating the OFF (no transmission) condition and FIG. 4B the ON (transmission) condition of the individual pixel cell.
Figure 4B:
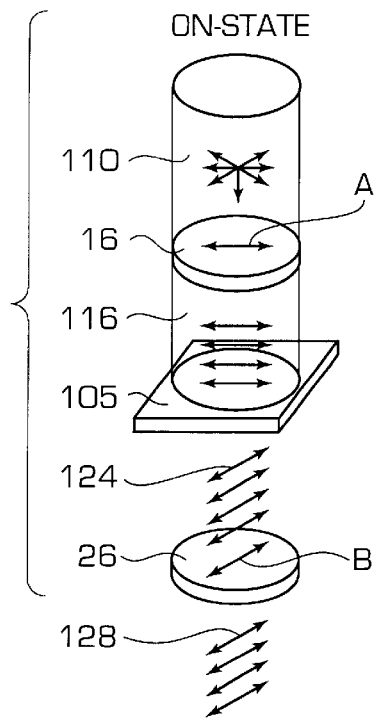
Figure 4C:
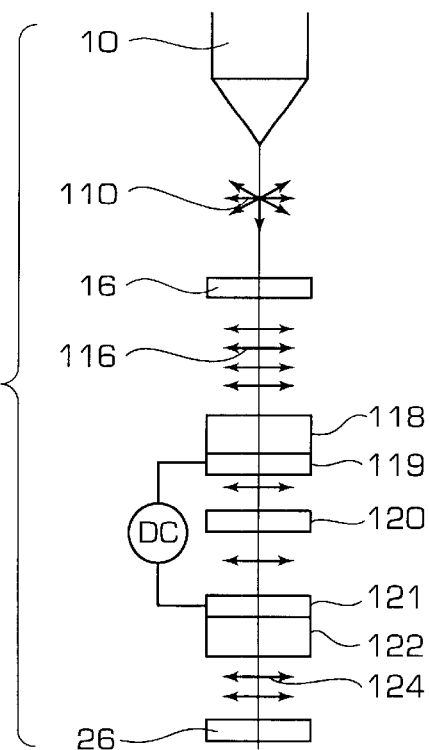
FIGS. 4C and 4D provide an electro-optical representation of the on/off transmission states for a pixel cell within the active matrix mask with FIG. 4C showing the OFF state (no transmission) and FIG. 4D showing the ON (transmission) state.
Figure 4D:
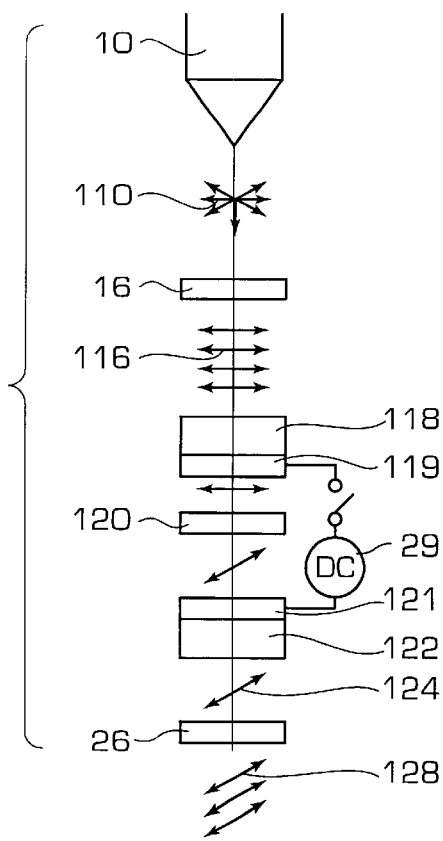

FIGS. 4A to 4D further illustrate a preferred arrangement of controllable matrix system 102 (FIG. 1) of the present invention, with FIGS. 4A and 4B providing an optical representation of the on/off transmission states for a pixel cell within matrix 22 (FIG. 3A) in conjunction with schematically illustrated first and second polarizers 16 and 26. FIGS. 4C and 4D provide an electro-optical representation of the on/off transmission states for a pixel cell within matrix 22.

FIGS. 4A and 4C illustrate the "off" state, while 4B and 4D illustrate the "on" state for the same pixel matrix segment section 105. In FIGS. 4B and 4D the unpolarized light 110 from excimer laser 10 is shown as being polarized along polarization vector A in similar fashion as shown in 3A. When no voltage is applied to the pixel cell associated with the pixel array segment section shown in FIG. 4B and 4D, the polarized UV light passing through the liquid crystal material of matrix 22 is twisted 90° while going through the mask as represented by the resultant twisted polarized UV light 124 exiting the mask 22. In the illustrated embodiment of FIG. 4B, the analyzer or second polarizer 26 has a polarization vector that coincides with the resultant twisted polarized UV light 124 such that the UV light is free to pass through the analyzer and on toward the projecting zone for ablation of the desired ablation volume segment In the case of the "on" state shown in FIGS. 4B and 4D, the pixel segment section 105 of matrix 22 represented in FIG. 4B will be transparent.

As shown in FIGS. 4A and 4C, the incoming unpolarized excimer light 110 is directed through first polarizer 16 having a polarizing vector represented by arrow A. Thus, the light exiting polarizer 16 in FIGS. 4A and 4C assumes the polarizing orientation of polarization vector A as similarly shown by the polarized UV light representation 116 in FIG. 3A. In passing through the twisted nematic crystal material, the polarized UV light of FIGS. 4A and 4C is not twisted 90° because an electric voltage has been applied and the liquid crystal molecules align with the electrical field such that the twisted nematic physical effect is lost due to the realignment of liquid crystal molecules. Thus, the UV polarized light 124 exiting the matrix segment section 105 is blocked by analyzer 26 as the polarization vector B of analyzer 26 is not coincident with the polarization vector of the polarized UV light 124. Thus, this pixel segment section 105 of matrix 22 will appear dark in its blocking mode.

With reference now to FIGS. 7, 8A to 8F and 9A–9F, a discussion is provided of a preferred ablation sequence involving ablating volumetric ablation segments from an exposed cornea to achieve a desired cornea sculpturing (e.g., a LASIK procedure) using the mask system 102 (FIG. 1) in conjunction with a laser system such as laser system 100 (FIG. 1). For simplifying the discussion, the pixels 125 (FIG. 6) in array 122 (FIG. 5) will be treated as each having either a fully "on" (100% duty cycle) or a fully "off" (0° duty cycle) state during the pulse period of the main laser and with each matrix reconfiguration being made to coincide with the master pulse sequence of the excimer laser beam such that the array changes once between each pulse and each pixel cell is maintained fully on or off with a given array for the full pulse period.

In other words, each pixel is maintained on for the full pulse period rather than switching a transmitting pixel to a blocking state at some point prior to completion of the pulse duration. Also, with respect to FIGS. 8A to 8F, and in similar fashion to the presentation in FIG. 3A, the pixel grouping(s) which allow for transmission of the laser energy to the exposed corneal are shown by lighter areas 123 in each array of mask 22 while the blocking pixels 125 are shown by darker shading in mask 22.

Figure 7:
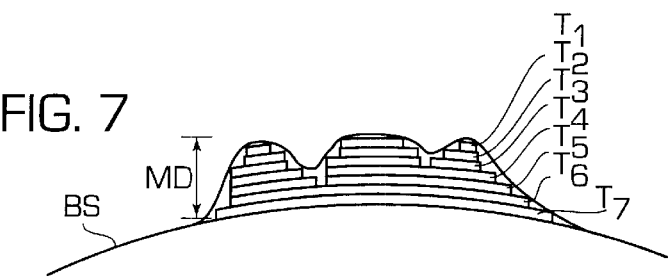
FIG. 7 shows a crossectional view through a cornea of a patient having an irregular topography, a schematic depiction of a best clinical sphere lying below the lower extremities of the irregular surface, and the cumulative ablation volume removed by way of a plurality of laser pulse transmission through different patterns provided in the active matrix mask.

FIG. 7 shows a schematic visual image of a customized volumetric ablation pattern data set that has been formed, such as in a manner described in U.S. patent application Ser. No. 09/267,926 to Dr. Luis Antonio Ruiz which application is incorporated herein by reference. FIG. 1 also shows topographer 50 and aberrometer 52 which are useful either alone or in combination in determining the desired volumetric ablation pattern data set for achieving the desired resultant ablation volume in the cornea. Regular ablation patterns used commonly for myopic, hyperopic, and astigmatism treatment (e.g.,from a library of stored volumetric ablation volume patterns) can also be relied upon (either alone or in combination with different treatment requirements) in forming the desired three dimensional volumetric ablation volume pattern. In addition, the present mask system and laser system are also well suited for ablations directed at presbyopia treatment such as described in U.S. Pat. Nos. 5,533,997; 5,928,129; and PCT/US99/26242 each to Dr. Luis Antonio Ruiz and each incorporated herein by reference.

While the borders of clear regions 123 (e.g., FIG. 8A) are shown as being entirely smooth curvatures there would be some degree of stepped edging in view of the pixel array. However, with an n×m pixel array (see FIG. 5) of, for example, 1024×1024 cells and with each preferably being square shaped with 100$\mu$ or less sides a very fine resolution peripheral contour would be formed in any ablated material.

Figure 8A:
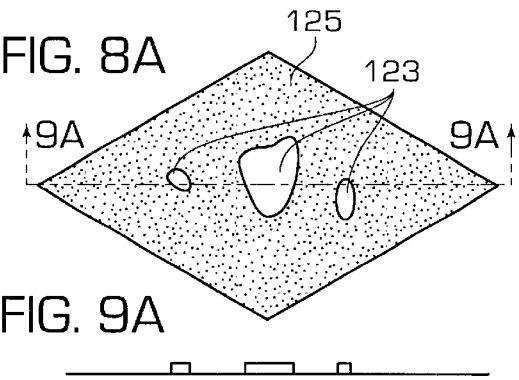
FIGS. 8A to 8F each provide a schematic illustration of six different patterns formed in the active matrix mask in sequence and between laser pulse applications.

FIGS. 8A to 8D show six different matrix array patterns that are each set based on a switch over time period (in this embodiment, the matrix switch time is made in one-to-one correspondence with the pulse duration of the laser). As shown by FIGS. 8A and 9A the pixel array is set so as to remove the volume of material lying above reference line T1 (FIG. 7) during a first laser pulse of the polarized large beam. FIG. 8A shows the pixel matrix array setting (e.g., an array of 1024×1024 with a 100 $\mu$ square size) for achieving the ablation volume removal segment lying above reference line T1. FIG. 9A shows a schematic presentation of an ablation segment that would be removed following a laser beam pulse application through the mask and to the projected surface.

Figure 8B:
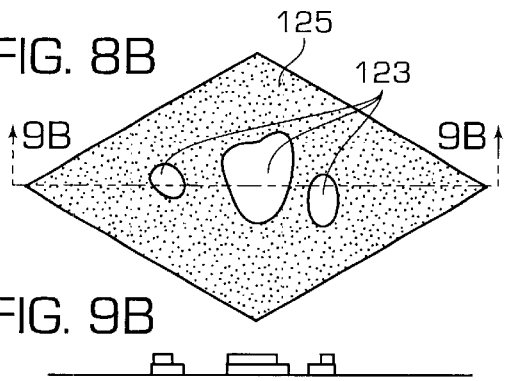
Figure 9A:
FIGS. 9A to 9F show a crossectional view of the volumetric ablation volume segment (corresponding to the matrix segment generated by the process) being removed upon transmission of a laser pulse (or a common number of pulses) with FIGS. 9B–9F showing cumulative ablation segments taken along the corresponding cross-sections in FIGS. 8B to 8F.
Figure 9B:
Figure 8C:
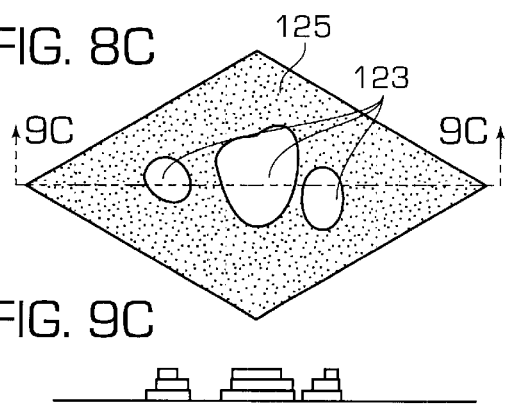
Figure 8D:
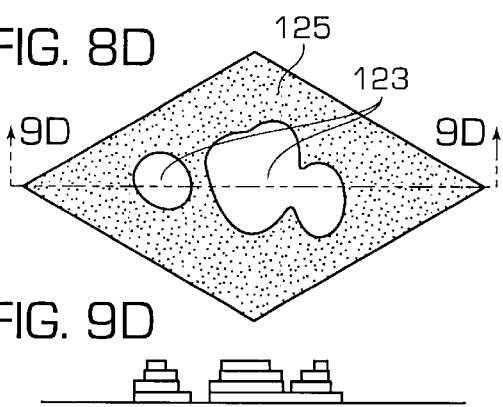
Figure 9C:
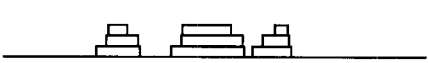
Figure 9D:
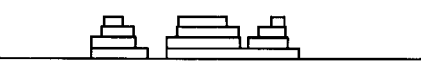
Figure 8E:
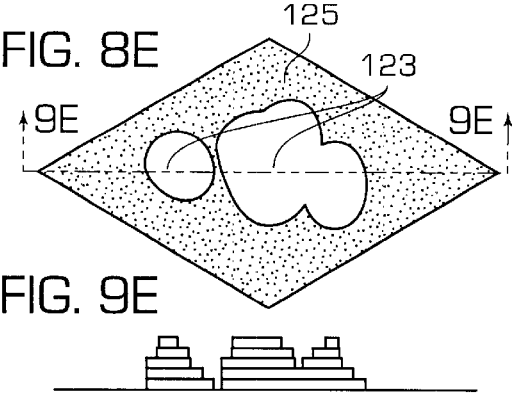
Figure 9E:
Figure 8F:
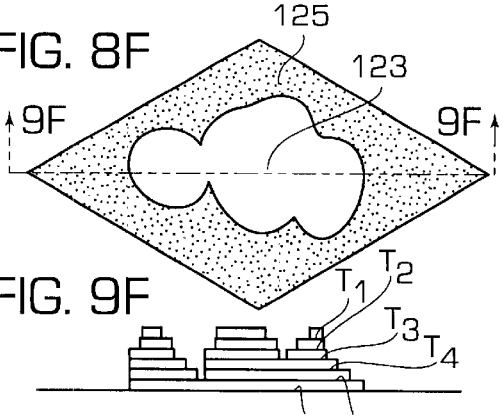
Figure 9F:
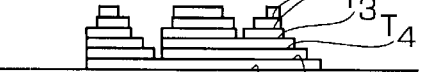
Figure 10:
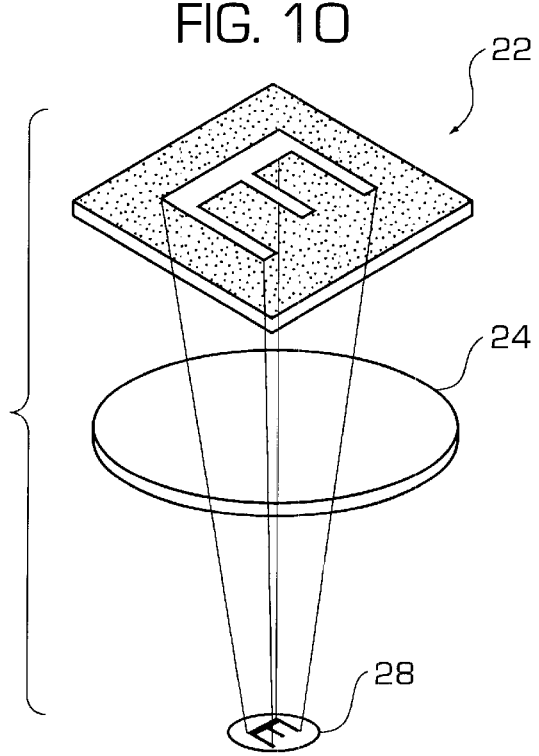
FIG. 10 shows a schematic view of the UV light beam exiting the active mask and being focused and the corresponding ablation pattern (the letter "E", used instead of a regular or irregular corneal topography to simplify the explanation) being projected onto a projecting surface.
Figure 11A:
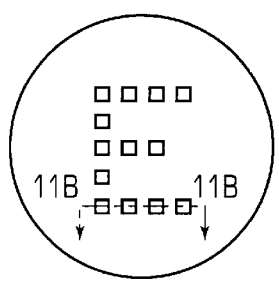
FIG. 11A shows a close up view of the ultraviolet energy application in FIG. 10 on the cornea with the transmitted energy from the spaced apart pixels of the matrix being placed in a spaced apart arrangement on the ablation plane or projected surface.
Figure 12A:
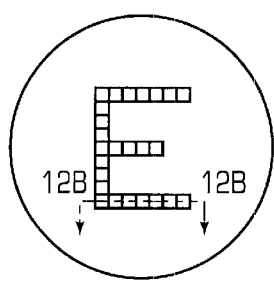
FIG. 12A shows the ablation pattern provided on the projected surface with the individual pixels forming a non-overlapping, non-spaced (abutting) ablation.
Figure 13A:
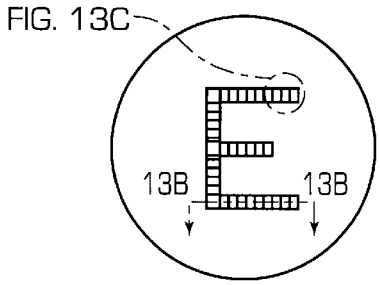
FIG. 13A shows an excess overlap arrangement in the ablation pattern imposed on the cornea.
Figure 11B:
FIG. 11B shows the ablation layer cross-section pattern along cross-section lines 11B—11B in FIG. 11A and the ridges formed by under-ablation registration between the focused transmitted energy and the projecting surface.
Figure 12B:
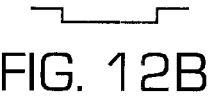
FIG. 12B shows the ablation layer cross-section pattern along cross-section line 12B—12B in FIG. 12A, showing a smooth perfect ablation.
Figure 13B:
FIG. 13B shows the ablation layer cross-section pattern along cross-section lines 13B—13B in FIG. 13A showing spikes formed by over-ablation registration caused by overlapping the focused transmitted energy with respect to the projecting surface.
Figure 13C:
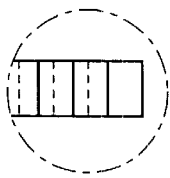

FIG. 8B shows the pixel matrix array setting for achieving the ablation volume removal segment (predetermined by processor 32 following receipt of the overall desired volumetric ablation volume pattern data for the cornea being ablated as in the segment above T1) lying between reference lines T1 and T2 in FIG. 7. FIG. 9B illustrates schematically the cumulative effect of removal of the ablation volume segments by the laser beam for two setting cycles of the matrix array. Similarly, FIG. 8C shows the pixel matrix array setting for achieving the ablation segment lying between reference lines T3–T2 with FIG. 9C showing the cumulative volumetric effect of the three represented different pixel matrix array settings. Pair sets 8D–9D; 8C–9C; 8F–9F show additional matrix array settings and the corresponding cumulative volumetric ablation following application of the laser beam pulse with FIG. 8D directed at the ablation segment defined between reference lines T4–T3, FIG. 8E directed at the ablation segment defined by reference lines T5–T4, FIG. 8F directed at the ablated segment defined by reference lines T6–T5 The ablation segment T7–T6 in FIG. 7 is represented by the pixel pattern 123 shown in FIG. 3A with the stacked ablation segments lying above the best clinical sphere (representation BS in FIG. 7) intended to correspond with the topographical plan view of the three dimensional volumetric ablation pattern represented in FIG. 3C taken along cross-section lines 7—7 in FIG. 3C. The best clinical sphere BS shown in FIG. 7 represents the desired final, resculptured profile for the exposed cornea believed to be best suited for that particular patient such as the technique explained in the aforementioned U.S. patent application Ser. No. 09/267,926 filed Mar. 10, 1999 by Dr. Luis Antonio Ruiz.

As can be seen from a comparison of FIGS. 8A–8F, for this volumetric ablation volume pattern being removed, the volumetric ablation segments expand and merge together in going from a removal of the outer exposed corneal topographical (z-axis) extremities toward the predetermined best clinical sphere BS reference line (in cross-section) lying below the irregularities. As the laser pulse applications are cumulative, the sequence of pattern settings could be altered (e.g., starting with the configuration of FIG. 8F and working in reverse and working in sequence back to 8A or even a mixed application of array sets 8A to 8F).

Also, while FIG. 7 shows an over exaggerated extension of cornea tissue in a central region above the best clinical sphere, reference line BS could also represent the initial outer exposed cornea surface profile wherein a series of ablations based on conventional, preestablished volumetric ablation profiles such as in correcting myopia, hyperopia and astigmatism (or presbyopia as discussed above are ablated). For instance, generally circular, centralized ablation segments can be imposed upon the cornea to achieve a conventional corrective myopic central cap reduction in the center region of the cornea. Also, as a typical ablation depth for an excimer laser pulse is 0.25$\mu$, the number of ablation stacks would generally be much larger in number than the schematic representation in FIGS. 8A–8F (e.g., a number in the few hundreds corresponding with the aforementioned number of large spot laser beam pulses typically required to achieve typical diopter corrections).

Thus, upon completion of the preset number of different pixel array settings and laser pulse applications following the matrix resettings, a removed volumetric ablation pattern conforming to the predetermined volumetric ablation pattern determined by an analysis of the eye is achieved with high precision like a flying spot laser but with the avoidance of the time delays and overlapping problems associated with a flying spot laser. In addition, there is provided a multi-use matrix array which can be used for handling a plurality of different patient ablation requirements while using a speedier large beam application; but without the complexities of the previous mechanical fixed mask arrangements or the erodible masks of the prior art. Moreover, the laser system of the present invention provides for high resolution, extremely smooth walls and avoids ridge and valley formation due to excessive overlap.

Figure 14:
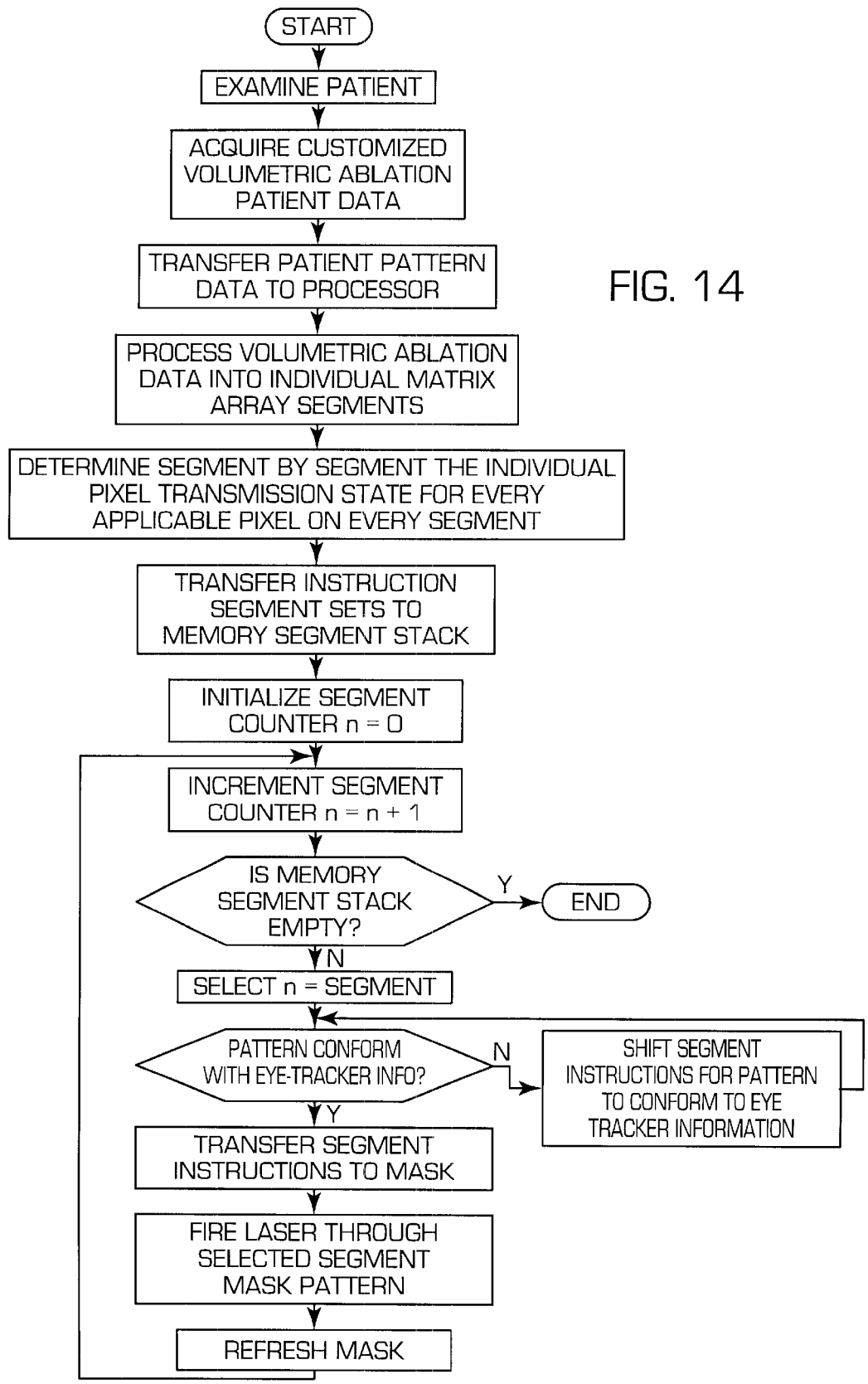
FIG. 14 provides a flow diagram of a method of utilizing the laser system of the present invention for performing a controlled ablation on a substrate.

FIG. 14 provides a flow chart illustrating a sequence of steps in carrying out a volumetric ablation removal technique such as that represented by FIGS. 8A to 8F.

FIG. 14 shows, in addition to the sequence of steps for carrying out a volumetric ablation removal sequence, some preliminary steps which are carried out prior to initiation of the volumetric ablation removal sequence. In an initial preliminary step, the patient is examined to determine what type of ablation requirements might exist. An applicable volumetric ablation pattern data set is subsequently formed or acquired which best suits the individual needs of the patient. Reference is again made to U.S. Ser. No. 09/267,926 which discusses in additional detail some of the various concerns and some of the applicable techniques for acquiring an ablation pattern data set, although any other conventional technique for determining desired ablation volumes to be ablated can be utilized under the present invention.

The acquired volumetric ablation pattern data set for the ablation deemed best suited for the patient (48) (e.g., a matrix of x, y, z values conforming to the volume of cornea lying between a best clinical sphere and the analyzed topography of the cornea and/or the volume based on aberrometer determined characteristics of the different optical components and shapes of the eye by, for example, use of topographer (50) and/or aberrometer (52)). This information is sent to a suitable processor such as main computer 32. In a preferred embodiment, the received data set is broken down into volumetric ablation segments which preferably conform to a predetermined laser ablation depth defined by the laser characteristics and the laser energy densities utilized. This can be seen in a review of FIG. 7 which illustrates, in schematic fashion, stacked individual volumetric ablation segments which, in the cumulative, remove with high precision the ablation volume defined by the acquired volumetric ablation pattern data fed to the processor.

The processor then determines, for each volumetric ablation segment, the desired individual pixel array settings required to satisfy the desired volumetric ablation segment profile for the applicable ablation segment. For example, with an x, y, z corneal topograph matrix data set as the acquired customized volumetric ablation pattern data, the processor, based on the maximum and minimum z-axis points in the data set, determines the maximum distance (MD) FIG. 7 between the same points and, based on the a blation characteristics of the laser beam (maximum ablation depth) (LD), breaks down the maximum distance (MD) into a number (N) of z-axis ablation segments that corresponds to the formula MD=LD×N with N equal to the pulses×the duty cycle ratio (which is preferably 1:1 for the above described embodiment).

With a typical corneal laser ablation depth of 0.21 $\mu$ to 0.25 $\mu$ and a preferred pixel window of between 100 to 150 $\mu$ (per side) a very high precision capability is attained both with respect to ablation depth and with respect to peripheral or x-y plane boundary profiling. With an ablation depth value of 0.21 $\mu$ or 0.25 $\mu$ and pixel size of 100 $\mu$ to 125 $\mu$ per side, it is possible to achieve under the present invention a resolution of, for example, 1/50th of a diopter, extremely smooth ablation surfaces, no (±0.75% with respect to pixel size) overlap or spacing, or essentially no (±1 to 5%) overlap or spacing, and a very high accurate registration between the desired volumetric ablation pattern and the actually ablated volume. Also, because of the very small ablation depth (0.21 $\mu$ to 0.25 $\mu$) each matrix array cycle (preferably in a 1 to 1 ratio with respect to the laser pulse cycle), any deviation (due to N not being a whole number integer) in having MD=LD×N would still allow for higher precision contouring.

As further shown by FIG. 14, after the volumetric ablation data is broken down into individual ablation formation segments, the processor then determines the individual pixel transmission state for every pixel in every segment. For example, a review of the corneal volume representation of the acquired volumetric ablation data set for a chosen matrix array segment is made and the pixel settings for achieving the corneal volume representation is implemented (i.e., setting to "on" those pixels which correspond in location to the matrix array segment for laser beam transmission, while placing all others in the matrix array in a blocking state). While a direct feed following each determination of the required pixel transmission state for an ablation segment to an activated mask is possible, it is preferable to store in a memory stack each individual matrix array data set for each of the individual matrix array segments (also described as an ablation segment). Each matrix array data set is assigned a number and then an ablation process is initiated wherein one of the numbered matrix array data sets is chosen and its information transferred (e.g., through computer interface 34 which transfers, for example, pixel on/off data representations into voltage pulse on/off voltage signals so as to achieve the desired overall pixel state for the matrix array). The laser beam is then fired through the selected, activated mask pixel array and directed on toward the cornea to be sculptured. Preferably the mask is varied between a preexisting state and a new state corresponding with the chosen segment between each pulse and with the "switch over" timing being achieved between laser shots, although it is also possible to carry out a number of pulses on the same matrix array setting prior to switching over to the next matrix array depending on, for example, the z-axis height of each segment. Also, for a sufficiently long laser pulse duration or a continuously applied electromagnetic radiation source, the duty cycle for an "on" pixel can be made less than 100% to accommodate any relative difference in material to be ablated along a common ablation volume segment's lower reference line. This would alter the number of on/off switch overs per laser pulse.

Also, in one embodiment of the invention, the resetting of the mask includes first setting all pixels within the array to a common "off" position and then placing those pixels which are to be "on" in an on setting while leaving the other pixels unchanged (or vice versa if the resetting involves switching all to "on" initially). The former arrangement is preferable, as the resetting of all to "off" between the switching over to the next desired array pattern provides an additional safety blocking screen.

In an alternate embodiment, the previous mask setting is maintained and a comparison is made via the processor between the chosen matrix array set and the preexisting matrix array set to determine which pixels require change over and which can stay the same. This can lessen the number of individual pixel setting changes, particularly in situations wherein the next segment has many pixel settings in common with an earlier setting as in FIGS. 8A–8F illustrating a situation where the later pixel setting segment generally builds upon an earlier setting by expanding out the x-y plane ablation profile pixel representation (or in an opposite matrix array segment processing).

As further shown by FIG. 14, the cycle of switching the matrix arrays from a prior to a new setting and firing the laser is repeated until it is determined that each memory segment has been implemented and that the memory segment stack is empty. The timing between mask refreshings in accordance with a preferred embodiment of the present invention is preferably less than 100 milliseconds (ms) and more preferably less than 50 ms with the range of 25 to 50 ms being well suited for many applications of the present invention. The invention's mask refreshing cycle is synchronized with the "on" main laser pulse, and also individual pixel cells can be controlled separately within the main laser pulse duration to achieve multiple on/off pixel modes during the laser pulse period and the synchronized refreshing period, if applicable.

As described above, pixels that are in a transmitting state can be left "on" for the full time period of the synchronized laser pulse to achieve the characteristic full ablation depth of the laser beam's pulse. This relationship can be seen by a comparison of FIGS. 15A and 15B wherein the laser pulse duration P is in an on state for the entire main laser pulse period (corresponding with the laser energy passage time period) as represented by the darkened region $R_1$ in FIG. 15B. FIG. 15B represents a 100% duty cycle with respect to the laser pulse period P. On the other hand, a pixel that is maintained entirely in an "off" state (not shown) during the laser pulse period P would thus have a 0% duty cycle (and no pulse representation).

To achieve an intermediate degree of ablation in sub-areas within an ablated segment area during pulse period P, the duty cycle can be varied from pixel to pixel by switching the duty cycle of respective pixels in a present matrix array. For example, FIG. 15C shows a 50% duty cycle where a respective pixel cell is switched from a transmission "yes" state to a transmission "no" state so as to be on for 50% of the pulse period P. In this way a partial ablation is carried out relative to the capability of a 100% duty cycle period which is shown in FIG. 15C during the first half of the pulse period but could also be applied during the last half of the pulse period (or refreshing period) or an intermediate period of the pulse period as well to achieve a 50% duty cycle.

FIGS. 15D and 15E illustrate even smaller duty cycles of 25% and 12.5%, respectively. Adjacent each duty cycle pulse prevention, there is schematically illustrated the corresponding ablation depth for that duty cycle.

The upper portion of FIG. 15F schematically illustrates the different ablation percentages made possible during one of the repetitive laser pulse periods, while the lower half shows the corresponding degree of ablation carried out on an underlying substrate. Thus, with a varying of the individual duty cycle within a particular matrix array a variation in depth of ablation can be achieved with respect to the underlying substrate. Whether a duty cycle of less than 100% can be utilized will depend upon the time of the laser pulse period. The duty cycle manipulation would provide advantageous flexibility and precision (considered above and beyond the capability of switching individual voltage levels within the pixels in a given matrix set). This flexibility and added precision being made possible by varying the duty cycle amongst pixels in a particular pixel array set is also applicable to a variety of fields including for example, photoresist and photolithography applications, and with a variety of electromagnetic radiation sources including pulsed or continuously supplied electromagnetic radiation providers such as a xenon lamp, a mercury vapor lamp or the like.

With reference again to FIGS. 1 and 2, some additional preferred features for laser system 100 are discussed. To properly focus the exposure of the matrix transmitted laser beam onto the projecting zone, non-ablating lasers are preferably used. For example, two HeNe lasers such as a red HeNe laser (39) with a wavelength of about 632.8 nm and a Green HeNe laser (40) with a wave length of about 543.5 nm, respectively, are preferred for alignment with a third HeNe laser (20) of about 632.8 nm used for patient fixation. As the third HeNe laser is used for patient fixation, it must be aligned with the patient eye and the alignment lasers. Additionally, to accurately control X, Y pattern exposure registration on the patient cornea, an infrared eye tracker system (36) is used to compensate patient eye movement during an ablation procedure. The eye tracker system monitors the center of the cornea (or some other fixed point) and assures that the UV light beam is precisely projected to the target area of the cornea following any eye movement.

Under the present invention, to achieve correlation between the laser beam application and a patient shifted projecting zone as determined by eye tracker 36, the eye tracker outputs data to a processor such as processor 32 and the shift parameters provided by the eye tracker are processed by the processor and fed to the active pixel array in the form of signals to alter the pixel array pattern x-y reference coordinates whereupon an appropriate shift in the on/off states of the pixel array assigned for producing the latent image(s) for forming the ablation segment is made.

In this way, a deviation in the patient's eye can be accommodated by the present invention, without the need for mechanically moving components which can wear out or jam (each which can produce serious implications in a surgical procedure). While the avoidance of any mechanical moving components is preferred through use of electronic pixel shifting to achieve a shifted transmission configuration in the active mask, the present invention can also include an assembly comprising turning mirror 21, active mask 22, focusing lens 24 and polarizer 26 that can be implemented as a unit, and with an electronically driven moveable support or the like, the center axis of the projected beam can be maintained at the same location on the eye despite the eye movement picked up by the eye tracker (e.g., angular movement together with x-y plane movement of the unit).

Figure 16:
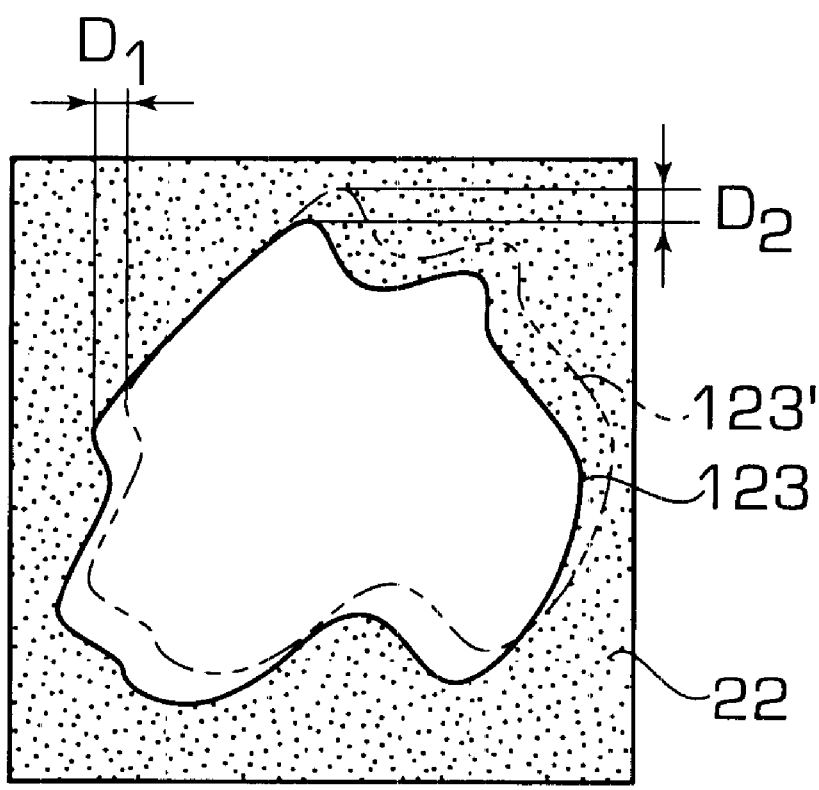
FIG. 16 shows a depiction of electronic active mask eyetracker compensation on the x, y axis.

FIG. 16 schematically illustrates a shifting in the mask array pattern to accommodate a shift in the projected zone of a substrate to be ablated with the shifting being measured by substrate monitoring means which conveys shift information to a processor, which in turn controls the mask to initiate a new setting prior to the next energy application. Thus, with respect to a laser system as shown in FIG. 1, the transmission pattern 123 is shifted (in conjunction with a shift determined by the eye tracker 36 and shift information processed by main computer 32 and relayed through interface 34) to new pattern position 123' in mask 22, to properly place the applied energy on the shifted cornea.

FIG. 16 also shows lengths D1 and D2 representing shifting distances in the image presented by the mask along the x-y plane of the matrix 22. If D1 or D2 exceed a preset standard (e.g., a shift beyond a 3 to 5 mm acceptable outer limit range on the main computer or too many pixels out in an array having to be shifted) the processor can initiate a laser shut down through use of beam shutter 14.

FIGS. 1 and 2 illustrate the use of a video camera system (37) provided to show the patient's eye in a color monitor (38). Initial positioning of patient is realized by a microprocessor controlled bed (46) that responds to commands generated by a joystick (44) which moves the patient bed on the axes X, Y and Z and interlocks the patient bed when the surgery is in progress. The patient bed is also interfaced with the main computer via computer interface (42). As earlier noted, prior to surgery, the patient (48) is accurately examined by a topographer (50) or an aberrometer (52) or any other type of medical device for analyzing the optical structure of the eye, and the information generated by the analyzer is then transferred to the main computer (32) which processes the information and generates the customized cornea ablation pattern deemed best suited by the surgeon for achieving the desired correction. The analyzer of the eye characteristics information can be a component of the overall system or can be a remote sub-system with the volumetric ablation pattern data set deemed best suited for that patient being stored by the main computer either by way of a direct feed to the main computer from the patient acquisition exam or stored on an appropriate storage medium for transfer to an input of the main computer, or transferred remotely from one location to another through any suitable information transmission means such as a telephone line.

Although the present invention has been described with reference to preferred embodiments, the invention is not limited to the details thereof. Various substitutions and modifications will occur to those of ordinary skill in the art following a review of this application, and all such substitutions and modifications are intended to fall within the spirit and scope of the invention as defined in the appended claims.

What is claimed is:

1. A mask system for controlling the transmission of ultraviolet electromagnetic radiation (UV), comprising:
   a first UV grade polarizer;
   a patternable liquid crystal mask having a plurality of individual pixels with individually adjustable states of transmission with respect to polarized UV electromagnetic radiation received from said first UV grade polarizer;
   a second UV grade polarizer positioned for receipt of polarized UV electromagnetic radiation transmitted through said liquid crystal mask.

2. A mask system of claim 1 further comprising a processor interfaced with said liquid crystal patternable mask for controlling relative transmission states between said individual pixels.

3. The mask system of claim 1, further comprising a beam expander/collimator assembly receiving the UV electromagnetic radiation and positioned upstream, with respect to UV electromagnetic radiation travel, of said liquid crystal mask.

4. The mask system of claim 3, wherein said beam expander/collimator is positioned downstream, with respect to UV electromagnetic radiation travel, of said first polarizer.

5. The mask system of claim 4, further comprising a focusing lens positioned downstream, with respect to UV electromagnetic radiation travel, of the liquid crystal mask and upstream of said second polarizer.

6. The mask system of claim 1 wherein said liquid crystal mask includes a twisted nematics liquid crystal material.

7. The mask system of claim 1 wherein said first and second polarizers are physically separated from said liquid crystal mask.

8. The mask system of claim 1 wherein said mask comprises an inner and an outer UV grade substrate.

9. The mask system of claim 8 wherein said UV grade substrate is a material selected from a group consisting of UV grade synthetic fused silica or sapphire.

10. The mask system of claim 1 further comprising a processor interfaced with said liquid crystal mask for controlling relative transmission states between said individual pixels, and said processor comprising means for shifting a pattern formed in said liquid crystal mask in conjunction with a shift in a substrate to receive UV electromagnetic radiation transmitted by said liquid crystal mask.

11. The mask system of claim 1 wherein said first and second polarizers are designed for peak polarization of UV electromagnetic radiation at 193 nm wavelength.

12. The mask system of claim 1 wherein said mask involves a pixel array having at least 512×512 resolution with pixel size of 100 $\mu$ or less.

13. The mask system of claim 12 wherein said resolution is at least 1024×1024 in number.

14. The mask system of claim 1 wherein said individually adjustable states of transmission are limited to fully transmitting on and fully blocking off.

15. The mask system of claim 14 wherein said liquid crystal mask is designed for receipt of laser pulses and said mask system further comprises pixel switching timing means for timing pixel switching between different pixel states that is in a one-to-one relationship with respect to laser pulses received by said mask.

16. The mask assembly of claim 1 wherein said mask further comprises a pixel switching timing means for timing individual pixel switching between different states and which switching timing means sets a duty cycle for individual pixels at 0% to 100% with at least one set duty cycle being at an intermediate value falling between 0 to 100%.

17. A laser system for ophthalmological surgery, comprising:
    a laser;
    a liquid crystal mask having a plurality of individual pixels positioned for receiving a laser beam output by said laser; and said individual pixel cells having adjustable transmission states for forming a transmission pattern with respect to the laser beam received from said laser, and said laser system further comprising a processor with means for processing acquired ablation volume data of an eye and basing pixel control outputs to said mask on the proceeded acquired ablation volume data.

18. The laser system as recited in claim 17 further comprising a first UV grade polarizer positioned upstream with respect to laser beam travel to said pixels and a second UV grade polarizer positioned downstream with respect to laser beam travel from said pixels.

19. The laser beam as recited in claim 18 wherein liquid crystal material of said liquid crystal mask is a twisted nematic liquid crystal material.

20. The laser system as recited in claim 19 wherein said first polarizer and second polarizer have a common polar vector direction.

21. The laser system as recited in claim 19 wherein said first polarizer and said second polarizer have a non-common polar vector direction.

22. The laser system as recited in claim 17, further comprising a first polarizer positioned upstream of said mask and a laser beam expander/collimator assembly positioned downstream with respect to said first polarizer and upstream with respect to said liquid crystal mask.

23. The laser system as recited in claim 17 wherein said liquid crystal mask includes first and second substrates of a UV grade material.

24. A laser system as recited in claim 22 further comprising a focusing member positioned downstream from the liquid crystal mask.

25. A laser system as recited in claim 24 wherein said focusing member is designed to focus a latent image pattern formed by said mask to a projected surface wherein adjacent transmitting pixels are compressed into an essentially non-overlapping relationship involving less than 5% edge to edge overlap.

26. The laser system as recited in claim 17 further comprising directing means for directing pixel transmission state controls to said mask.

27. The laser system as recited in claim 26 wherein said directing means includes an interface linking said processor and mask, and said directing means refreshes a pattern in said mask on a fresh cycle of 100 ms or less.

28. The laser system as recited in claim 17 further comprising means for acquiring ablation volume data of an eye.

29. The laser system of claim 28 wherein said means for acquiring ablation volume data of an eye includes means for determining corneal ablation topographical data.

30. The laser system of claim 29 wherein said means for acquiring ablation volume data of an eye includes an aberrometer and a topographer.

31. The laser system of claim 17 wherein said processor includes means for segmenting acquired corneal volumetric ablation pattern data into plurality of segments and means for determining a desired individual pixel transmission status arrangement for respective segments of said acquired and segmented volumetric ablation pattern.

32. The laser system of claim 31 further comprising means for sequentially changing a pixel array pattern based on a predetermined pixel transmission status for each of said segments.

33. The laser system of claim 17 further comprising an interface, with said processor being in communication with said mask via said interface device, and said interface device including means for converting digital information to individual pixel voltage signals.

34. The system of claim 17 wherein said processor includes means for determining a transmission switching rate for individual pixels of said mask based on a duty cycle correlated with a laser pulse of said laser.

35. The laser system of claim 34 wherein said individual pixels of said mask are assigned either a duty cycle of 0% representing no transmission state during the laser pulse period or a 100% full transmission state during the laser pulse period.

36. The laser system of claim 34 wherein at least some of said individual pixels of said mask are assigned a duty cycle which is intermediate a 0% duty cycle representing a no-transmission state during the pulse period and a 100% duty cycle representing a full transmission state during the pulse period state.

37. The system of claim 17 further comprising an eye tracker and said processor being in communication with both said eye tracker and said mask, and said processor includes means for implementing a switch in a transmission state of individual pixel cells to shift a pattern defined by pixel cells in said mask from a first pattern position to a second pattern position in correspondence with a shaft in location of a projected surface of an eye being monitored by said eye tracker.

38. The system of claim 17 wherein said mask has a pixel array that is at least 1024×1024 in number with pixels being 100 $\mu$ or less.

39. A method for ablating an eye cornea comprising:
   directing a laser beam to a liquid crystal mask having a plurality of individually controllable pixels;
   directing transmitted portions of said laser beam exiting said mask onto a corneal surface for sculpturing the cornea.

40. The method of claim 39 further comprising altering a first pattern defined by said pixels into a second pattern between pulses of said laser.

41. The method of claim 39 further comprising processing acquired volumetric ablation pattern data to provide pixel transmission state control signals to said pixels of said mask.

42. A system for opthalmological surgery, comprising:
   a patternable liquid crystal mask with pixel cells having liquid crystal material;
   means for directing radiation through said mask for use in opthalmological surgery;
   means for varying the pattern of said mask; and
   a UV grade polarizer positioned upstream, with respect to radiation travel, to said mask.

43. A system as recited in claim 42, comprising a second UV grade polarizer positioned downstream from said mask.

44. A system as recited in claim 42, wherein said means for directing radiation includes a laser source which generates a laser beam and, between said laser source and an eye to be treated relative to laser beam travel, a collimator/expander, a turning mirror and a focusing device are positioned.

45. A system for opthalmological surgery, comprising:
   a patternable liquid crystal mask having liquid crystal material;
   means for directing radiation through said mask for use in opthalmological surgery;
   pattern varying means for varying a radiation transmission pattern in said mask; and
   an eye tracker in communication with said pattern varying means.

46. The system as recited in claim 45, wherein said pattern varying means includes a processing device and said eye tracker is in communication with said processing device.

47. The system as recited in claim 46, wherein said mask includes a plurality of liquid crystal pixel cells and said pattern varying means includes means for implementing a switch in a transmission state of individual pixel cells to shift a pattern defined by said pixel cells from a first pattern position to a second pattern position in correspondence with a shift in location of an eye.

48. A system for opthalmological surgery, comprising:
   a patternable liquid crystal mask with liquid crystal pixel cells for directing radiation through said mask for use in opthalmological surgery;
   means for varying the pattern of said mask; and
   means for acquiring ablation volume data of an eye which is in communication with said means for varying the pattern of said mask.

49. The system as recited in claim 48, wherein said means for acquiring ablation volume data includes a topographer.

50. The system as recited in claim 48, wherein said means for varying the pattern of said mask includes a processor and means for directing signals to vary the transmissivity level of said pixels.

51. The system as recited in claim 49, wherein said means for acquiring ablation volume data includes an interface which receives topographical data from said topographer and forwards the topographical data to said processor.

52. The system as recited in claim 48, wherein said means for acquiring ablation volume data includes an aberrometer.

53. The system as recited in claim 46, wherein said means for acquiring ablation volume date is in communication with means for manipulating ablation volume data into a plurality of data segments, in which data segments are communicated to said means for varying the pattern of said mask to implement a series of mask patterns conforming to the ablation volume data segments.

54. A laser system for opthalomological surgery, comprising:
   a laser;
   a liquid crystal mask having a plurality of individual pixels positioned for receiving a laser beam output by said laser; and said individual pixel cells having adjustable transmission states for forming a transmission pattern with respect to the laser beam received from said laser;
   a first UV grade polarizer positioned upstream with respect to the laser beam travel to said pixels and a second UV grade polarizer positioned downstream with respect to the laser beam travel from said pixels.

55. The laser system as recited in claim 54, wherein liquid crystal material of said liquid crystal mask is a twisted nematic liquid crystal material.

56. The laser beam as recited in claim 55 wherein said first polarizer and second polarizer have a common polar vector direction.

57. The laser beam as recited in claim 55 wherein said first polarizer and said second polarizer have a non-common polar vector direction.

58. A laser system for opthamological surgery, comprising:
   a laser;
   a liquid crystal mask having a plurality of individual pixels positioned for receiving a laser beam output by said laser; and said individual pixel cells having adjustable transmission states for forming a transmission pattern with respect to the laser beam received from said laser;
   a first polarizer position upstream of said mask and a laser beam expander/collinator assembly positioned downstream with respect to said first polarizer and upstream with respect to said liquid crystal mask.

59. A laser system for opthamological surgery, comprising:
   a laser;
   a liquid crystal mask having a plurality of individual pixels positioned for receiving a laser beam output by said laser; and said individual pixel cells having adjustable transmission states for forming a transmission pattern with respect to the laser beam received from said laser;
   wherein said liquid crystal mask includes first and second substrates of a UV grade material.

60. A laser system for opthamological surgery, comprising:
   a laser;
   a liquid crystal mask having a plurality of individual pixels positioned for receiving a laser beam output by said laser; and said individual pixel cells having adjustable transmission states for forming a transmission pattern with respect to the laser beam received from said laser;
   directing means for directing pixel transmission state controls to said mask.

61. The laser system as recited in claim 60, wherein said directing means includes a processor and an interface linking said processor and mask, and said directing means refreshes a pattern in said mask on a refresh cycle of 100 ms or less.

62. A laser system for opthamological surgery, comprising:
   a laser;
   a liquid crystal mask having a plurality of individual pixels positioned for receiving a laser beam output by said laser; and said individual pixel cells having adjustable transmission states for forming a transmission pattern with respect to the laser beam received from said laser;
   means for acquiring ablation volume date of an eye.

63. The laser system as recited in claim 62 wherein said means for acquiring ablation volume data of an eye includes means for determining corneal ablation topographical data.

64. The laser system of claim 63 wherein said means for acquiring ablation volume data of an eye includes an aberrometer and a topographer.

65. A laser system for opthalmological surgery, comprising:
   a laser;
   a liquid crystal mask having a plurality of individual pixels positioned for receiving a laser beam output by said laser; and said individual pixel cells having adjustable transmission states for forming a transmission pattern with respect to the laser beam received from said laser;
   a processor with said processor including means for segmenting acquired corneal volumetric ablation pattern into a plurality of segments and means for determining a desired individual pixel transmission status arrangement for respective segments of said acquired and segmented volumetric ablation pattern.

66. The laser system of claim 65 further comprising means for sequentially changing a pixel array pattern based on a predetermined pixel transmission status for each of said segments.

67. A laser system for opthamological surgery, comprising:
   a laser;
   a liquid crystal mask having a plurality of individual pixels positioned for receiving a laser beam output by said laser; and said individual pixel cells having adjustable transmission states for forming a transmission pattern with respect to the laser beam received from said laser;
   a processor and said processor including means for determining a transmission switching rate for individual pixels of said mask based on a duty cycle correlated with a laser pulse period of said laser.

68. The laser system of claim 67 wherein said individual pixels of said mask are assigned either a duty cycle of 0% representing no transmission state during the laser pulse period or a 100% full transmission state during the laser pulse period.

69. The laser system of claim 67 wherein at least some of said individual pixels of said mask are assigned a duty cycle which is intermediate a 0% duty cycle representing a no-transmission state during the laser pulse period and a 100% duty cycle representing a full transmission state during the pulse period state.

70. A laser system for opthamological surgery, comprising:
   a laser;
   a liquid crystal mask having a pularlity of individual pixels positioned for receiving a laser beam output by said laser; and said individual pixel cells having adjustable transmission states for forming a transmission pattern with respect to the laser beam received from said laser;
   an eye tracker and a processing device which is in communication with both said dye tracker and said mask, and said processing device includes means for implementing a switch in a transmission state of individual pixel shells to shift a pattern defined by pixel cells in said mask from a first pattern position to a second pattern in correspondence with a shift in location of a projected surface of an eye being monitored by said eye tracker.

71. A laser system for opthamological surgery, comprising:
   a laser;
   a liquid crystal mask having a plurality of individual pixels positioned for receiving a laser beam output by said laser; and said individual pixel cells having adjustable transmission states for forming a transmission pattern with respect to the laser beam received from said laser;
   wherein said mask has a pixel array that is at least 1024×1024 in number with pixels being 100 $\mu$ or less.

* * * * *